(12) United States Patent
Kline et al.

(10) Patent No.: US 8,124,828 B2
(45) Date of Patent: Feb. 28, 2012

(54) ATTACHMENT AREAS FOR WEARABLE ABSORBENT ARTICLES

(75) Inventors: Mark James Kline, Okeana, OH (US); Nezam Malakouti, Loveland, OH (US); John Glasgow Burns, Jr., Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 357 days.

(21) Appl. No.: 12/468,633

(22) Filed: May 19, 2009

(65) Prior Publication Data

US 2010/0298802 A1 Nov. 25, 2010

(51) Int. Cl.
*A61F 13/15* (2006.01)
(52) U.S. Cl. .. 604/378; 604/380; 604/381; 604/385.101
(58) Field of Classification Search .................. 604/378, 604/380, 381, 385.101
See application file for complete search history.

(56) References Cited

U.S. PATENT DOCUMENTS

| 3,981,306 A | | 9/1976 | Krusko |
|---|---|---|---|
| 4,701,176 A | | 10/1987 | Wilson et al. |
| 4,770,656 A | * | 9/1988 | Proxmire et al. ............. 604/393 |
| 2006/0009743 A1 | * | 1/2006 | Wang et al. ................... 604/365 |
| 2007/0123834 A1 | | 5/2007 | McDowall et al. |
| 2008/0004593 A1 | | 1/2008 | Lodge et al. |

FOREIGN PATENT DOCUMENTS

| EP | 0 274 753 A2 | 7/1988 |
|---|---|---|
| EP | 1 820 481 A1 | 8/2007 |
| WO | WO 94/07450 A1 | 4/1994 |
| WO | WO 02/34185 A1 | 5/2002 |

OTHER PUBLICATIONS

International Search Report & Written Opinion, PCT/US2010/035112, mailed Oct. 8, 2010, 14 pages.

* cited by examiner

*Primary Examiner* — Jacqueline F. Stephens
(74) *Attorney, Agent, or Firm* — Charles R. Ware

(57) ABSTRACT

A wearable absorbent article comprises an outer cover and an absorbent core assembly. At least a portion of the outer cover is joined to the absorbent core assembly over at least a first attachment area and a second attachment area. The overall lateral width of the second attachment area is less than the overall lateral width of the first attachment area. At least a portion of the second attachment area is disposed in a hip region of the article. The first attachment area is disposed longitudinally outboard from the second attachment area.

20 Claims, 14 Drawing Sheets

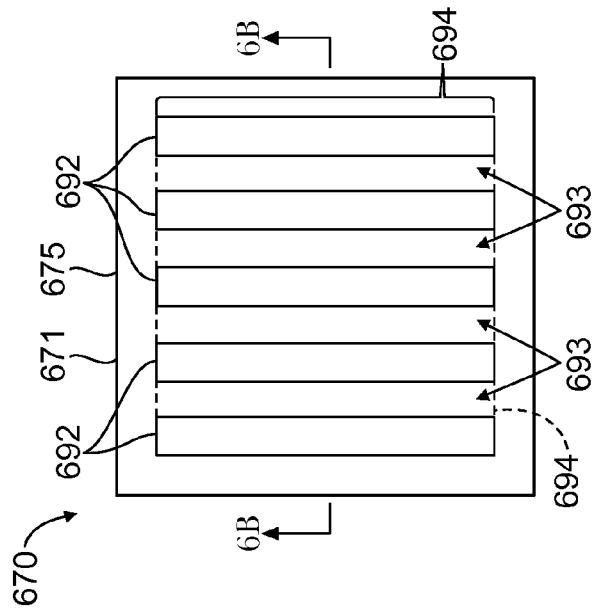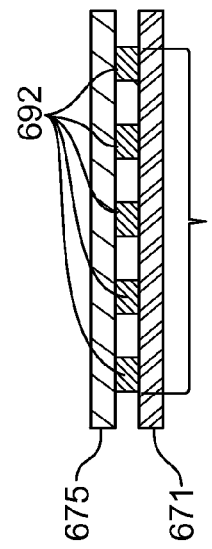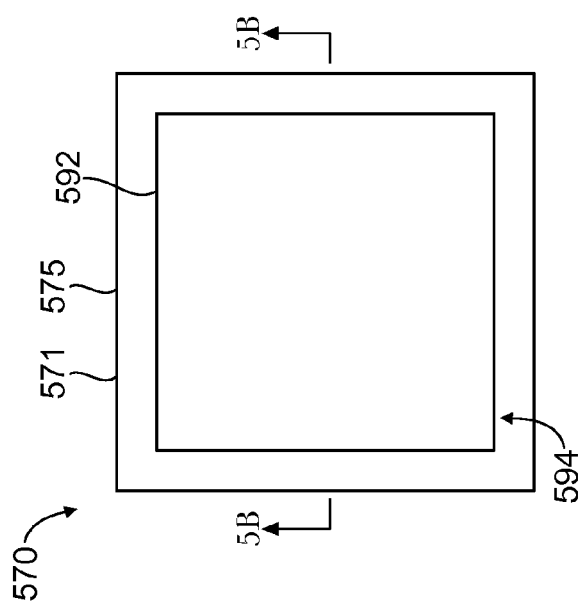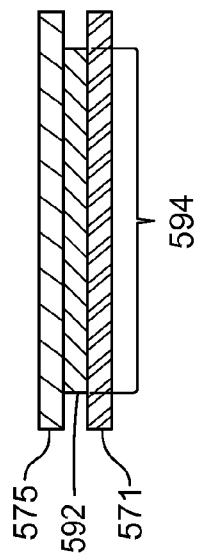

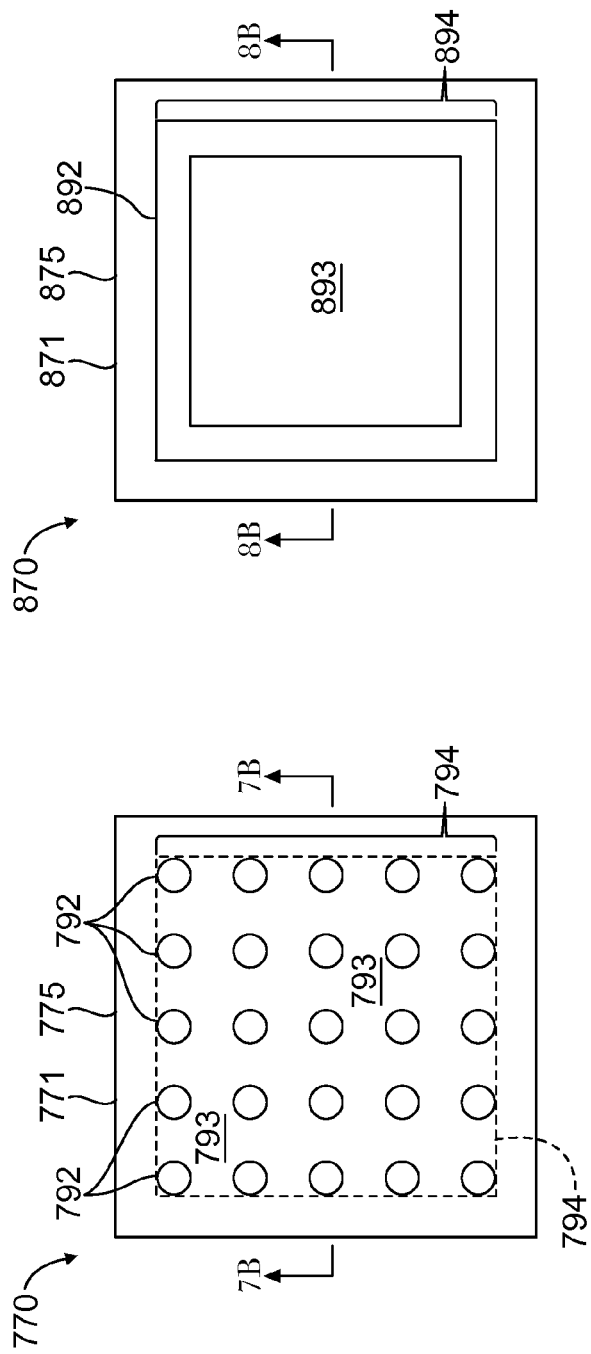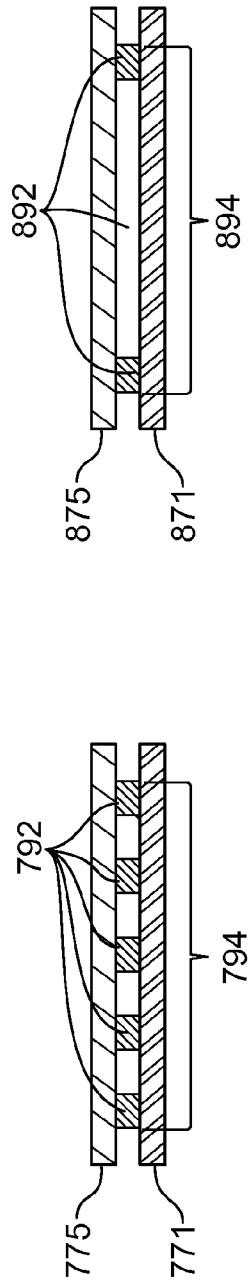

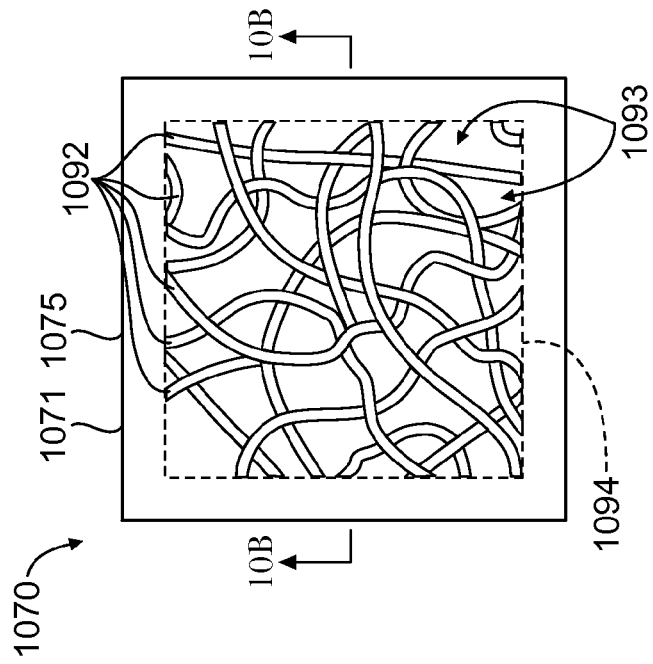
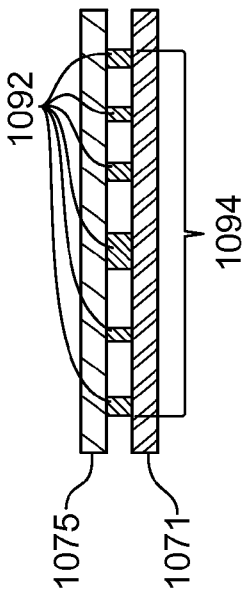
Fig. 10A
Fig. 10B
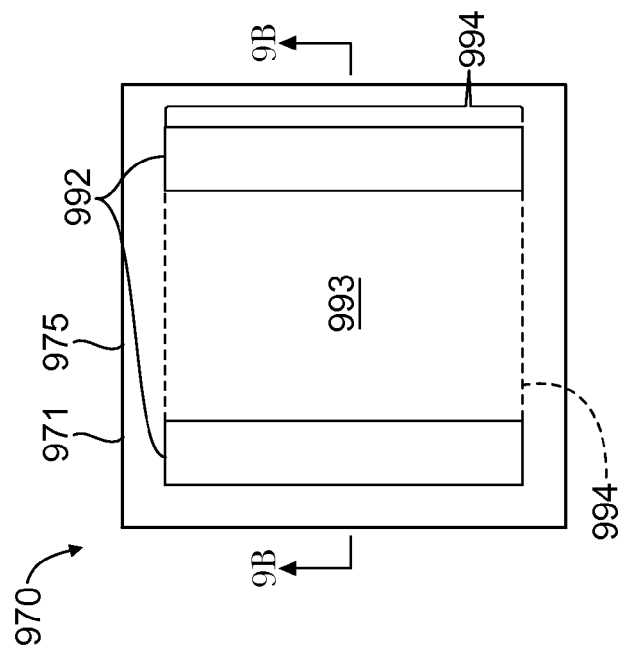
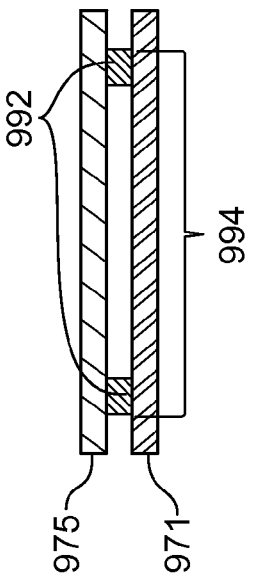
Fig. 9A
Fig. 9B

ATTACHMENT AREAS FOR WEARABLE ABSORBENT ARTICLES

FIELD

In general, embodiments of the present disclosure relate to wearable absorbent articles. In particular, embodiments of the present disclosure relate to wearable absorbent articles with stretchable outer covers.

BACKGROUND

Wearable absorbent articles include diapers and incontinence garments. Many wearable absorbent articles include outer covers, which form the outsides of the articles. It can be useful to make outer covers from stretchable materials, which can be extended in size. For example, a wearable absorbent article with a stretchable outer cover can be extended to fit a range of wearer sizes. A stretchable outer cover can also be extended to conform to a wearer's body as the wearer moves. Many wearable absorbent articles also include absorbent core assemblies to receive, contain, and absorb bodily wastes.

In order to provide structural integrity and support to an absorbent core assembly, the assembly can be joined to an outer cover. Unfortunately, if an absorbent core assembly is poorly joined to a stretchable outer cover, then the wearable absorbent article may not perform well. An absorbent core assembly that is overjoined to a stretchable outer cover may limit the degree to which the outer cover can be extended. The wearable absorbent article may look unattractive or feel uncomfortable. An absorbent core assembly that is underjoined to a stretchable outer cover may become improperly positioned within the article. An improperly positioned core assembly may extend out beyond a waist edge of the article, so the article looks unattractive. Also, an improperly positioned core assembly may have difficulty containing bodily wastes, resulting in leaks.

BRIEF DESCRIPTION OF THE DRAWINGS

FIG. 5A illustrates a portion of a wearable absorbent article with an absorbent core assembly joined to a portion of a stretchable outer cover over an attachment area, according to embodiments of the present disclosure.

FIG. 5B illustrates a cross-sectional view of the embodiment of FIG. 5A.

FIG. 6A illustrates a portion of a wearable absorbent article with a portion of an absorbent core assembly joined to a portion of a stretchable outer cover over an attachment area, according to embodiments of the present disclosure.

FIG. 6B illustrates a cross-sectional view of the embodiment of FIG. 6A.

FIG. 7A illustrates a portion of a wearable absorbent article with a portion of an absorbent core assembly joined to a portion of a stretchable outer cover over an attachment area, according to embodiments of the present disclosure.

FIG. 7B illustrates a cross-sectional view of the embodiment of FIG. 7A.

FIG. 8A illustrates a portion of a wearable absorbent article with a portion of an absorbent core assembly joined to a portion of a stretchable outer cover over an attachment area, according to embodiments of the present disclosure.

FIG. 8B illustrates a cross-sectional view of the embodiment of FIG. 8A.

FIG. 9A illustrates a portion of a wearable absorbent article with a portion of an absorbent core assembly joined to a portion of a stretchable outer cover over an attachment area, according to embodiments of the present disclosure.

FIG. 9B illustrates a cross-sectional view of the embodiment of FIG. 9A.

FIG. 10A illustrates a portion of a wearable absorbent article with a portion of an absorbent core assembly joined to a portion of a stretchable outer cover over an attachment area, according to embodiments of the present disclosure.

FIG. 10B illustrates a cross-sectional view of the embodiment of FIG. 10A.

SUMMARY

Figure 1A:
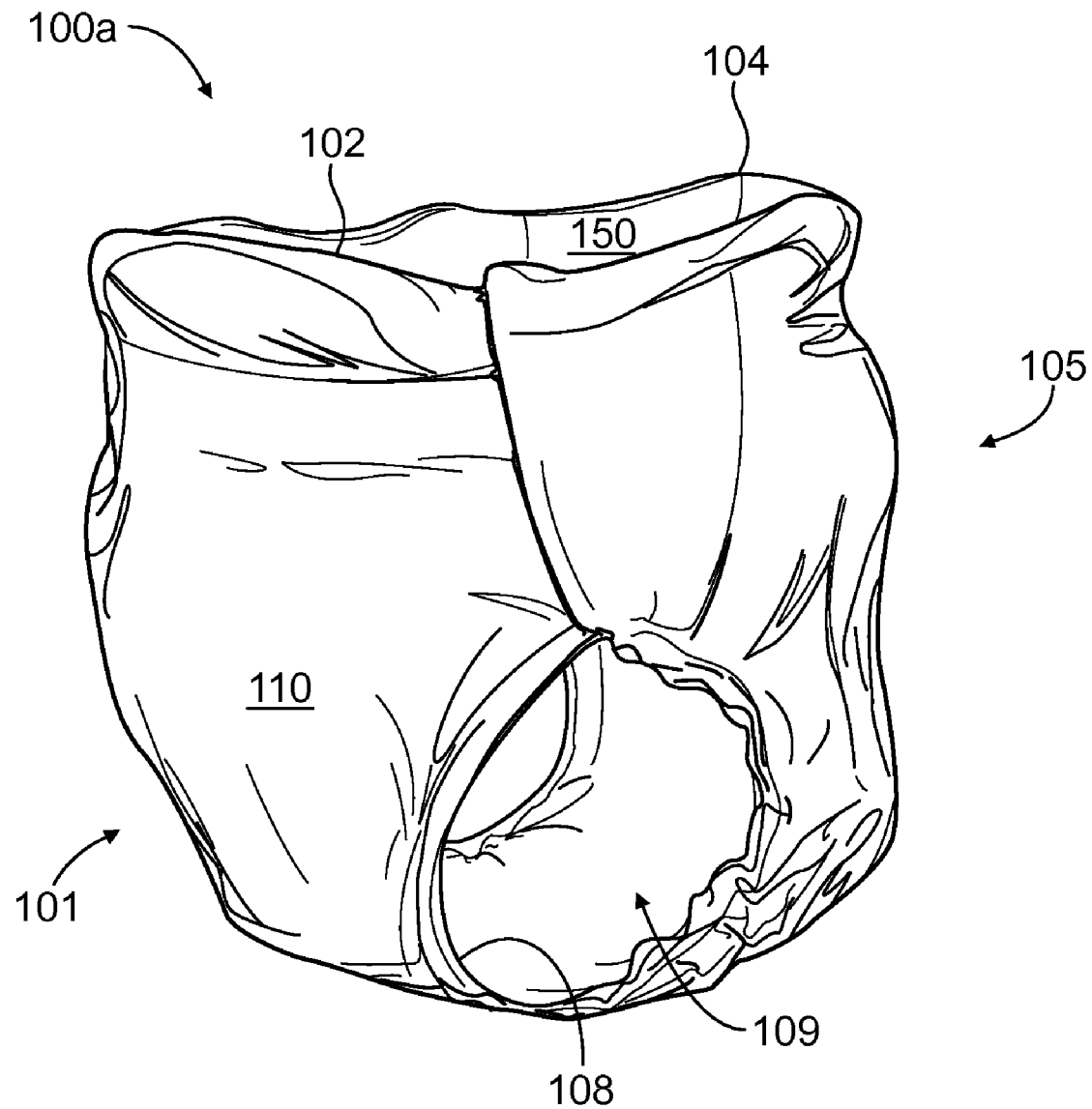
FIG. 1A illustrates a perspective view of a pant-type wearable absorbent article formed for wearing, including an absorbent core assembly joined to a stretchable outer cover, according to embodiments of the present disclosure.

The present disclosure includes wearable absorbent articles with absorbent core assemblies that are suitably joined to stretchable outer covers. While the absorbent core assemblies are provided with adequate structural integrity and support, the stretchable outer covers can also be extended to a significant degree because the absorbent core assemblies are joined to the stretchable outer covers by attachment areas that are strategically sized and placed within the articles.

As an example, a wearable absorbent article can have an absorbent core assembly and a stretchable outer cover. The absorbent core assembly can be joined to the stretchable outer cover by a wider first attachment area and a narrower second attachment area. The narrower second attachment area can be disposed in a hip region of the article, and the wider first attachment area can be disposed longitudinally outboard from the second attachment area.

The relatively wide width of the first attachment region, placed in a longitudinally outboard portion of the article, can provide adequate structural support for an end of the absorbent core assembly, where it is particularly useful. The relatively narrow width of the second attachment region, placed in the hip region of the article, can allow a significant degree of extensibility around a large circumference of a wearer's body, where it is especially beneficial. Thus, in wearable absorbent articles of the present disclosure, absorbent core assemblies are suitably joined to stretchable outer covers, such that the articles can look attractive and feel comfortable while being less likely to leak.

DETAILED DESCRIPTION

The attachment areas of the present disclosure can be used with all kinds of absorbent articles. An absorbent article can receive and absorb bodily exudates (e.g. urine, menses, feces, etc.). Examples of absorbent articles include products for sanitary protection and hygienic use.

Some absorbent articles are wearable. A wearable absorbent article is configured to be worn on or around a lower torso of a body of a wearer. Examples of wearable absorbent articles include diapers and incontinence undergarments. A wearable absorbent article can receive and contain bodily exudates while being worn by a wearer. Wearable absorbent articles can use embodiments of the present disclosure.

Some absorbent articles are disposable. A disposable absorbent article is configured to be wholly disposed of after a single use. A disposable absorbent article is configured such that the soiled article is not intended to be restored and reused (e.g., not intended to be laundered). Examples of disposable absorbent articles include feminine care products, such as pads and liners. Disposable absorbent articles can use embodiments of the present disclosure.

Some absorbent articles are reusable. A reusable absorbent article is configured to be partly or wholly used more than once. A reusable absorbent article is configured such that part or all of the article is durable, or wear-resistant to laundering, or fully launderable. One example of a reusable absorbent article is a diaper with a washable outer cover. Reusable absorbent articles can use embodiments of the present disclosure.

The figures of the present disclosure are intended to illustrate elements, their parts, and their relationships, as described in the specification; the figures are not intended to illustrate any particular relative or absolute size or dimension, unless otherwise stated in the text. The figures illustrate various wearable absorbent articles with attachment areas for joining absorbent core assemblies to stretchable outer covers, as described herein. For clarity, the figures do not illustrate all details of the articles. The attachment areas in FIGS. 1A-2C can be configured according to any of the embodiments of the present disclosure.

FIG. 1A illustrates a perspective view of a pant-type wearable absorbent article 100A formed for wearing, including an absorbent core assembly 150 joined to a stretchable outer cover 110, according to embodiments of the present disclosure. In various embodiments, the absorbent core assembly 150 can be joined to the stretchable outer cover 110 with attachment areas as described in connection with the embodiments of FIGS. 1B and 1C. The wearable absorbent article 100A also includes a front 101, a front waist edge 102, a back waist edge 104, a back 105, a leg opening edge 108, and a leg opening 109. A leg opening edge is a portion of a wearable absorbent article that forms part or all of a leg opening when the article is formed for wearing. In various embodiments, part, or parts, or all of a leg opening edge can include elastics to form a contractible leg opening. For the wearable absorbent article 100A, the leg opening edge 108 is a shaped cut-out, such that the wearable absorbent article 100A has an overall shape similar to an hourglass.

Throughout the present disclosure, a reference to a pant-type wearable absorbent article can refer to an embodiment that is fastenable or to an embodiment without fasteners. A reference to a pant-type wearable absorbent article can also refer to an embodiment of an article with one or more waist and/or leg openings that are preformed (i.e. formed during manufacture of the article) or to an embodiment of an article with waist and leg openings that are not preformed. Thus, each embodiment of an absorbent article of the present disclosure that is described as pant-type can be configured in any of these ways, as will be understood by one of ordinary skill in the art.

Figure 1B:
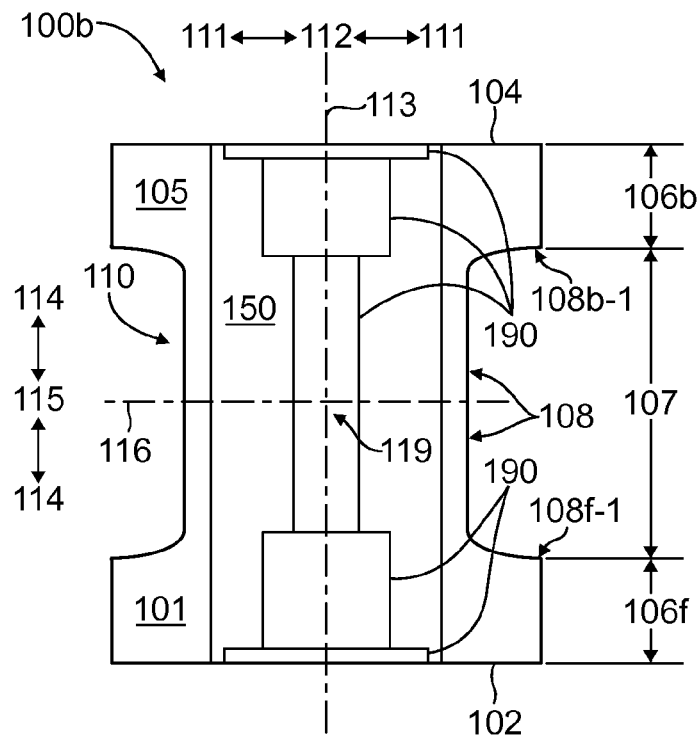
FIG. 1B illustrates a top view of an inside of a pant-type wearable absorbent article laid out in a flat and uncontracted state, including an absorbent core assembly joined to a stretchable outer cover, according to embodiments of the present disclosure.

FIG. 1B illustrates a top view of an inside of a pant-type wearable absorbent article 100B laid out in a flat and uncontracted state, including an absorbent core assembly 150 joined to a stretchable outer cover 110, according to embodiments of the present disclosure.

In FIG. 1B, a longitudinal centerline 113 and a lateral centerline 116 provide lines of reference for referring to relative locations of the wearable absorbent article 100B. The longitudinal centerline 113 runs between the waist edges of the article and separates the article into left and right halves. The lateral centerline 116 is perpendicular to the longitudinal centerline 113 and separates the front 101 from the back 105. When a first location is nearer to the longitudinal centerline 113 than a second location, the first location can be considered laterally inboard 112 to the second location. Similarly, the second location can be considered laterally outboard 111 from the first location. When a third location is nearer to the lateral centerline 116 than a fourth location, the third location can be considered longitudinally inboard 115 to the fourth location. Also, the fourth location can be considered longitudinally outboard 114 from the third location. The longitudinal centerline 113 and the lateral centerline 116 cross at a center 119 of the wearable absorbent article 100B.

FIG. 1B includes arrows indicating relative directions for laterally outboard 111, laterally inboard 112, longitudinally outboard 114, and longitudinally inboard 115, each with respect to the wearable absorbent article 100B. Throughout the present disclosure, a reference to a length or a longitudinal dimension, measurement, line, or direction refers to a dimension, measurement, line, or direction that is substantially or completely parallel to the longitudinal centerline 113 and a reference to a width or a lateral dimension, measurement, line, or direction refers to a dimension, measurement, line, or direction that is substantially or completely parallel to the lateral centerline 116. The terminology for describing relative locations, as discussed above, is used for wearable absorbent articles throughout the present disclosure, as will be understood by one of ordinary skill in the art.

The wearable absorbent article 100B includes a front 101, a front waist edge 102, a back waist edge 104, a back 105, a front hip region 106F, a back hip region 106B, a crotch region 107, and a leg opening edge 108.

A hip region is a portion of a wearable absorbent article disposed longitudinally outboard from a crotch region of the article and adjacent to a waist edge of the article. A front hip region is disposed in a front of a wearable absorbent article, adjacent to a front waist edge. A back hip region is disposed in a back of a wearable absorbent article, adjacent to a back waist edge.

A hip region has an overall longitudinal length that is a particular percentage of the pitch of the article. A wearable absorbent article has a pitch measured longitudinally between a farthest longitudinally outboard point on the front waist edge and a farthest longitudinally outboard point on the back waist edge. A hip region has an overall longitudinal length measured longitudinally from a farthest longitudinally outboard point on the adjacent waist edge to a point longitudinally inboard to the adjacent waist edge.

In various embodiments, a hip region can have an overall longitudinal length that is 35%, or 30%, or 25%, or 20%, or 15%, or 10% (or any integer value between any of these percentages) of the overall pitch of the article. The present disclosure contemplates that the various embodiments of attachment areas disclosed herein can be used with a hip region having an overall longitudinal lengths selected from any of the percentages described above.

In various embodiments, wherein a wearable absorbent article includes a clearly defined cut-to-shape leg opening edge, a hip region can, alternatively, be disposed longitudinally outboard from a farthest longitudinally outboard point of a leg opening edge and can have an overall longitudinal length measured longitudinally from a farthest longitudinally outboard point on the adjacent waist edge to the farthest longitudinally outboard point of the leg opening edge.

The wearable absorbent article 100B includes a farthest back longitudinally outboard point 108B-1 along the leg opening edge 108 and in the back 105. Thus, the back hip region 106B can be disposed longitudinally outboard from the farthest back longitudinally outboard point 108B-1 and can have an overall longitudinal length measured longitudinally from the farthest longitudinally outboard point on the adjacent waist edge 104 to the farthest back longitudinally outboard point 108B-1 of the leg opening edge 108. The wearable absorbent article 100B also includes a farthest forward longitudinally outboard point 108F-1 along the leg opening edge 108 and in the front 101. Thus, the front hip region 106F can be disposed longitudinally outboard from the farthest forward longitudinally outboard point 108F-1 and can have an overall longitudinal length measured longitudinally from the farthest longitudinally outboard point on the adjacent waist edge 102 to the farthest forward longitudinally outboard point 108F-1 of the leg opening edge 108.

Figure 1C:
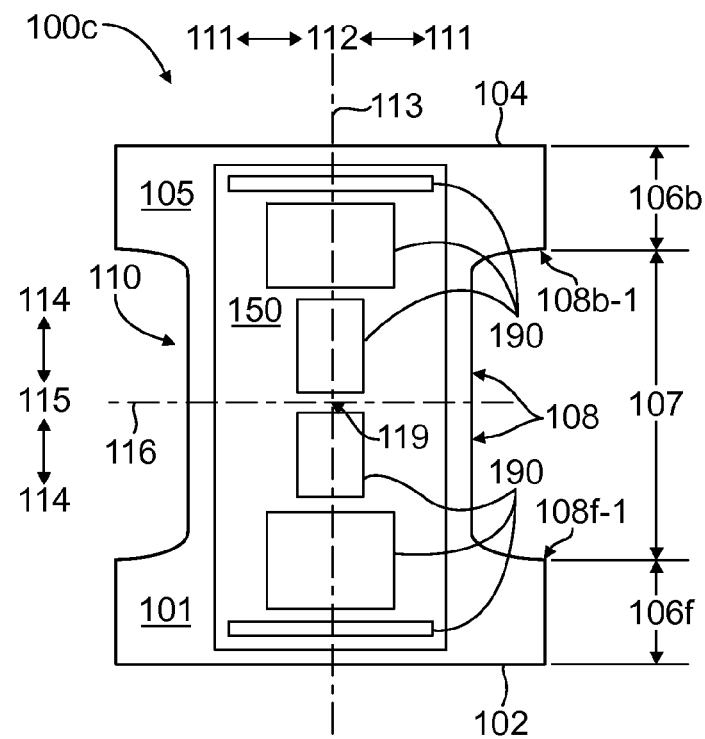
FIG. 1C illustrates a top view of an inside of a pant-type wearable absorbent article laid out in a flat and uncontracted state, including an absorbent core assembly joined to a stretchable outer cover, according to embodiments of the present disclosure.
Figure 1D:
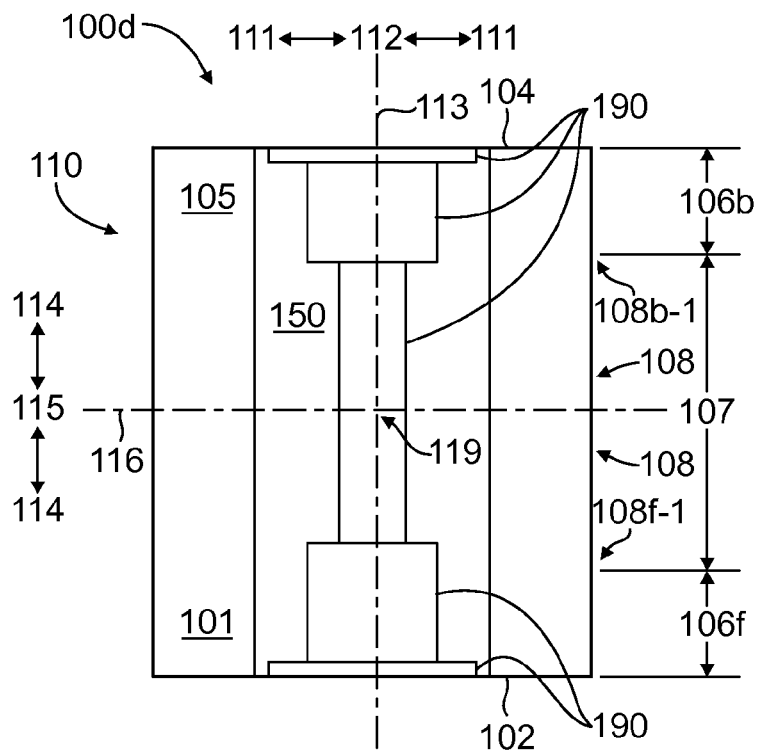
FIG. 1D illustrates a top view of an inside of a pant-type wearable absorbent article laid out in a flat and uncontracted state, including an absorbent core assembly joined to a stretchable outer cover, according to embodiments of the present disclosure.
Figure 1E:
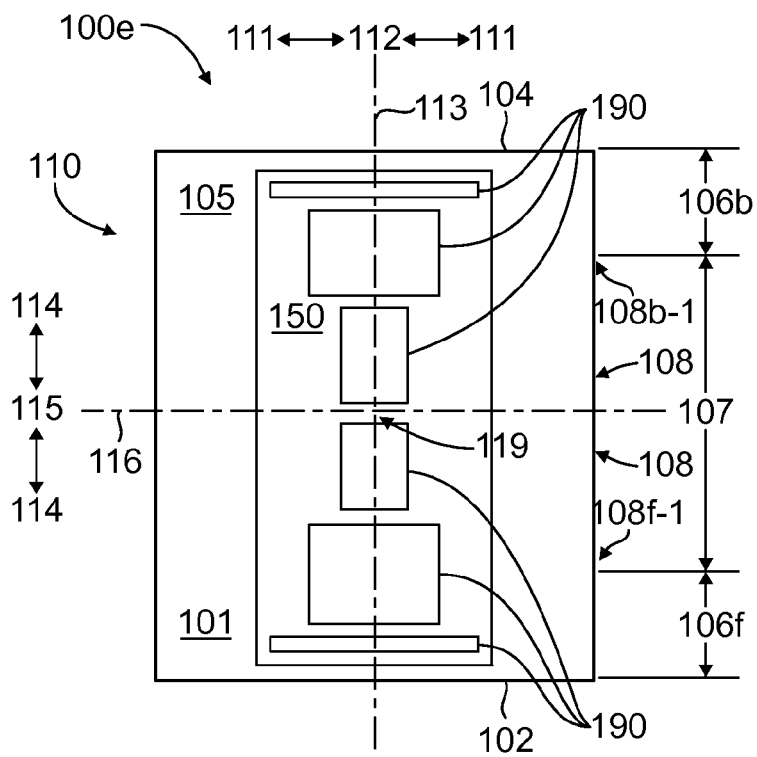
FIG. 1E illustrates a top view of an inside of a pant-type wearable absorbent article laid out in a flat and uncontracted state, including an absorbent core assembly joined to a stretchable outer cover, according to embodiments of the present disclosure.
Figure 1F:
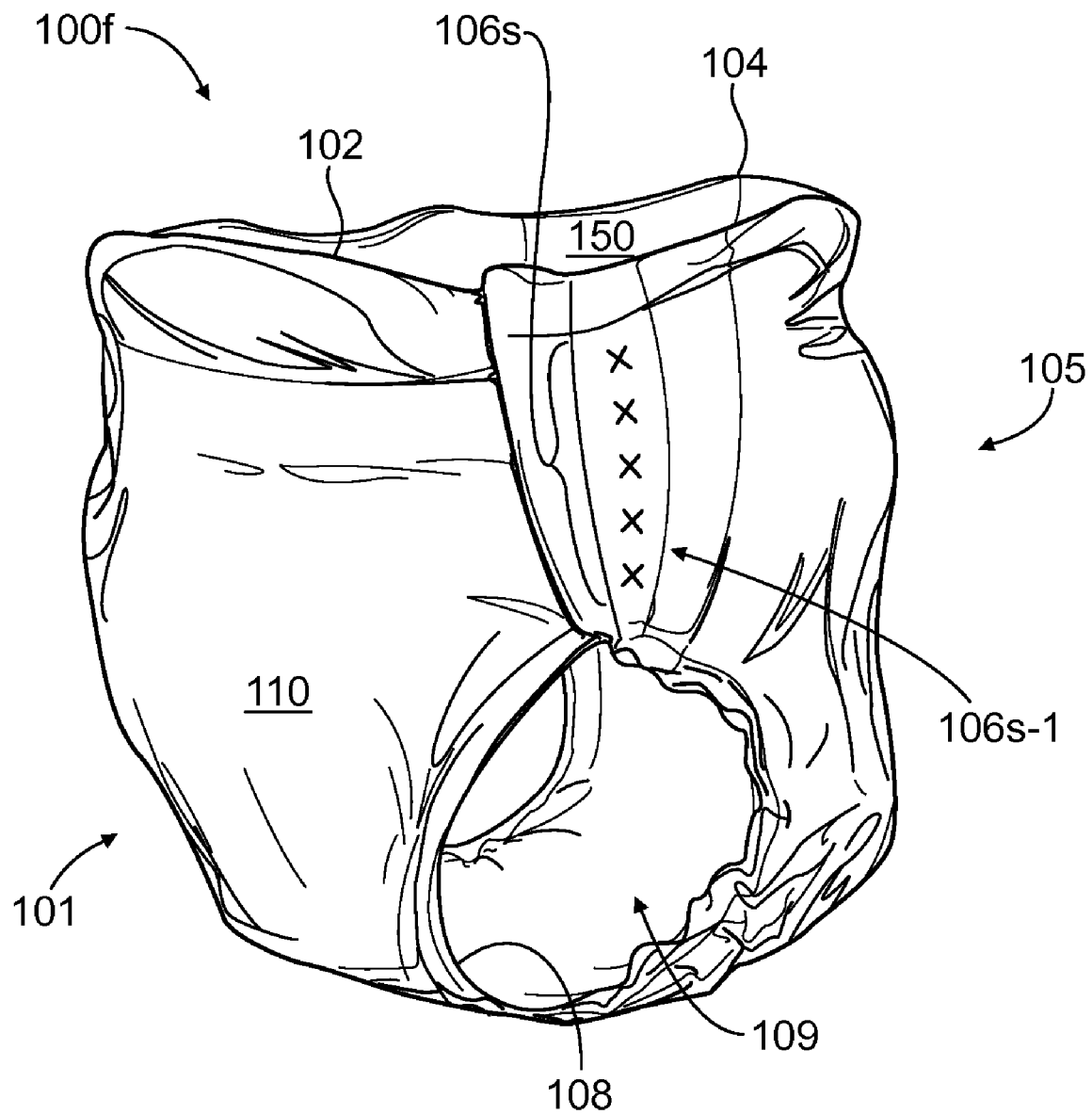
FIG. 1F illustrates a perspective view of a pant-type wearable absorbent article formed for wearing, including an absorbent core assembly joined to a stretchable outer cover, according to embodiments of the present disclosure.

In various embodiments, wherein a pre-formed pant-type article does not include a clearly defined cut-to-shape leg opening edge, a hip region can, alternatively, be disposed longitudinally outboard from a farthest longitudinally inboard point on a side connection and can have an overall longitudinal length measured longitudinally from a farthest longitudinally outboard point on the adjacent waist edge to the farthest longitudinally inboard point on the side connection, as described in connection with the embodiments of FIGS. 1D-1F.

In the wearable absorbent article 100B, the stretchable outer cover 110 is joined to the absorbent core assembly 150 over attachment areas 190. The outer cover 110, the absorbent core assembly 150, and the attachment areas 190 in FIG. 1B can each be configured as described in connection with the embodiment of FIG. 3A. In various embodiments of the wearable absorbent article 100B, the front 101, or the back 105, or the front 101 and the back 105, can be configured as described in FIG. 3A.

FIG. 1C illustrates a top view of an inside of a pant-type wearable absorbent article 100C laid out in a flat and uncontracted state, including an absorbent core assembly 150 joined to a stretchable outer cover 110, according to embodiments of the present disclosure. The wearable absorbent article 100C includes a front 101, a front waist edge 102, a back waist edge 104, a back 105, a front hip region 106F, a back hip region 106B, a crotch region 107, and a shaped leg opening edge 108. The wearable absorbent article 100C also includes a longitudinal centerline 113 and a lateral centerline 116 defining directions for laterally outboard 111, laterally inboard 112, longitudinally outboard 114, and longitudinally inboard 115, as well as a center 119. The outer cover 110, the absorbent core assembly 150, and attachment areas 190 in FIG. 1B can each be configured as described in connection with the embodiment of FIG. 4. In various embodiments of the wearable absorbent article 100C, the front 101, or the back 105, or the front 101 and the back 105, can be configured as described in FIG. 4.

FIG. 1D illustrates a top view of an inside of a pant-type wearable absorbent article 100D laid out in a flat and uncontracted state, according to embodiments of the present disclosure. Wearable absorbent article 100D is configured in the same way as wearable absorbent article 100B, except that, in the wearable absorbent article 100D, the leg opening edge 108 is a portion of a linear longitudinal edge, such that the wearable absorbent article 100A has an overall shape that is rectangular.

Also, the wearable absorbent article 100D includes a farthest back longitudinally outboard point 108B-1 along the leg opening edge 108 and in the back 105, wherein the farthest back longitudinally outboard point 108B-1 coincides with a farthest longitudinally inboard point on a side connection, as described in connection with the embodiment of FIG. 1F. Further, the wearable absorbent article 100D includes a farthest forward longitudinally outboard point 108F-1 along the leg opening edge 108 and in the front 101, wherein the farthest forward longitudinally outboard point 108F-1 coincides with a farthest longitudinally inboard point on a side connection, as described in connection with the embodiment of FIG. 1F.

FIG. 1E illustrates a top view of an inside of a pant-type wearable absorbent article 100E laid out in a flat and uncontracted state, according to embodiments of the present disclosure. Wearable absorbent article 100E is configured in the same way as wearable absorbent article 100C, except that, in the wearable absorbent article 100E, the leg opening edge 108 is a portion of a linear longitudinal edge, such that the wearable absorbent article 100A has an overall shape that is rectangular. The wearable absorbent article 100E also includes a farthest back longitudinally outboard point 108B-1 along the leg opening edge 108 and in the back 105, as well as a farthest forward longitudinally outboard point 108F-1 along the leg opening edge 108 and in the front 101, as described in connection with the embodiment of FIG. 1D.

FIG. 1F illustrates a perspective view of a pant-type wearable absorbent article 100F formed for wearing. In various embodiments, the wearable absorbent article 100F can be configured in the same way as wearable absorbent article 100D or 100E. The wearable absorbent article 100F is a pre-formed pant-type article that does not include a clearly defined cut-to-shape leg opening edge. However, the wearable absorbent article 100F includes a side connection 106S. In some embodiments, the side connection 106S can be durable or refastenable. The side connection 106C has a farthest longitudinally inboard point 106S-1.

Figure 2A:
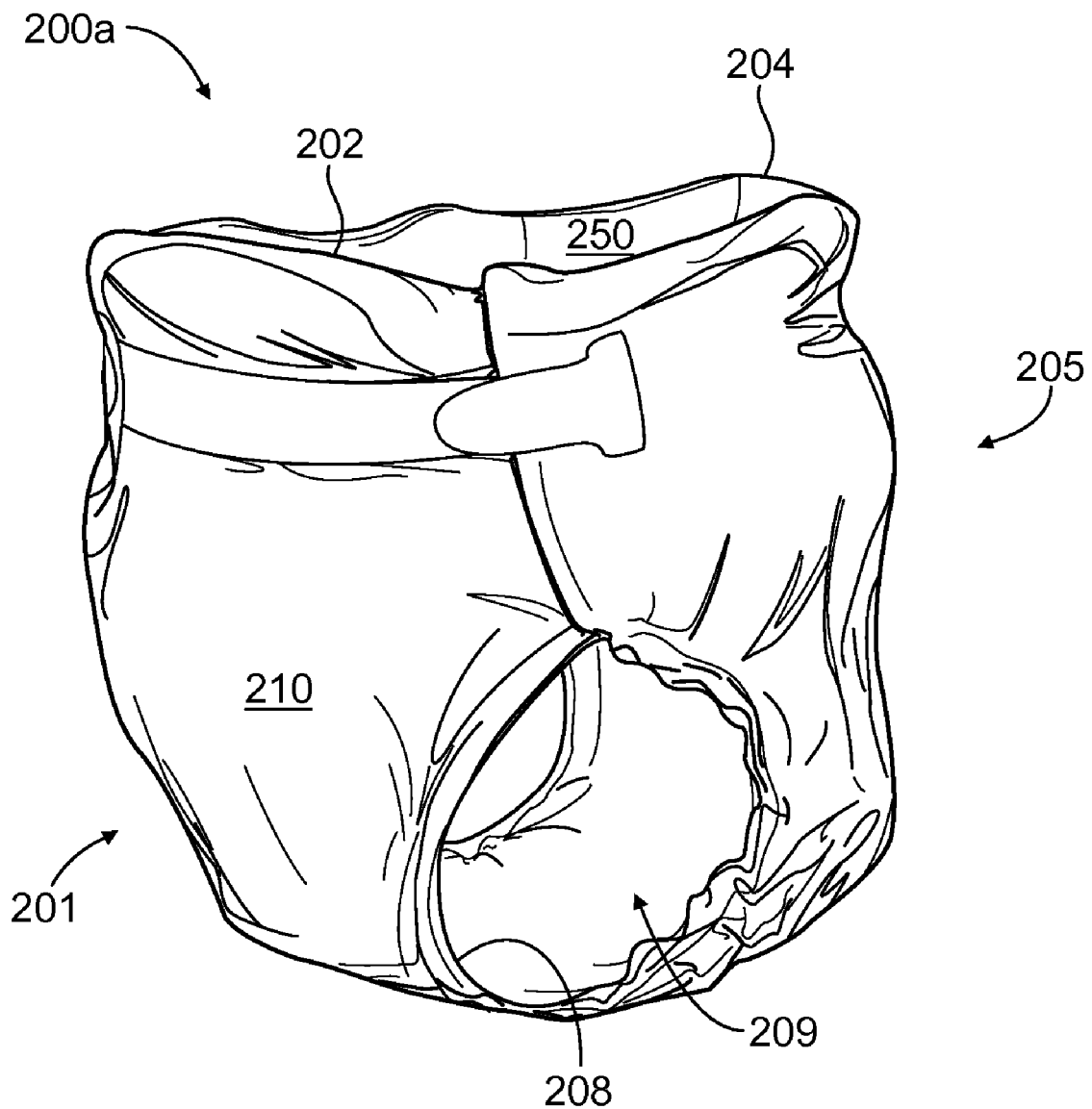
FIG. 2A illustrates a perspective view of a front-fastenable wearable absorbent article formed for wearing, including an absorbent core assembly joined to a stretchable outer cover, according to embodiments of the present disclosure.

FIG. 2A illustrates a perspective view of a front-fastenable wearable absorbent article 200A formed for wearing, including an absorbent core assembly 250 joined to a stretchable outer cover 210, according to embodiments of the present disclosure. In various embodiments, the absorbent core assembly 250 can be joined to the stretchable outer cover 210 with attachment areas as described in connection with the embodiments of FIGS. 2B and 2C. The wearable absorbent article 200A also includes a front 201, a front waist edge 202, a back waist edge 204, a back 205, a leg opening edge 208, and a leg opening 209.

While the present disclosure refers to front-fastenable wearable absorbent articles, the present disclosure also contemplates alternate embodiments of wearable absorbent articles having attachment areas, as described herein, wherein the wearable absorbent articles are rear-fastenable. Thus, each embodiment of a wearable absorbent article of the present disclosure that is described as front-fastenable can also be configured to be rear fastenable, as will be understood by one of ordinary skill in the art. Embodiments of the present disclosure can also be applied to various other wearable absorbent articles with other systems for holding the articles in place on wearers.

Figure 2B:
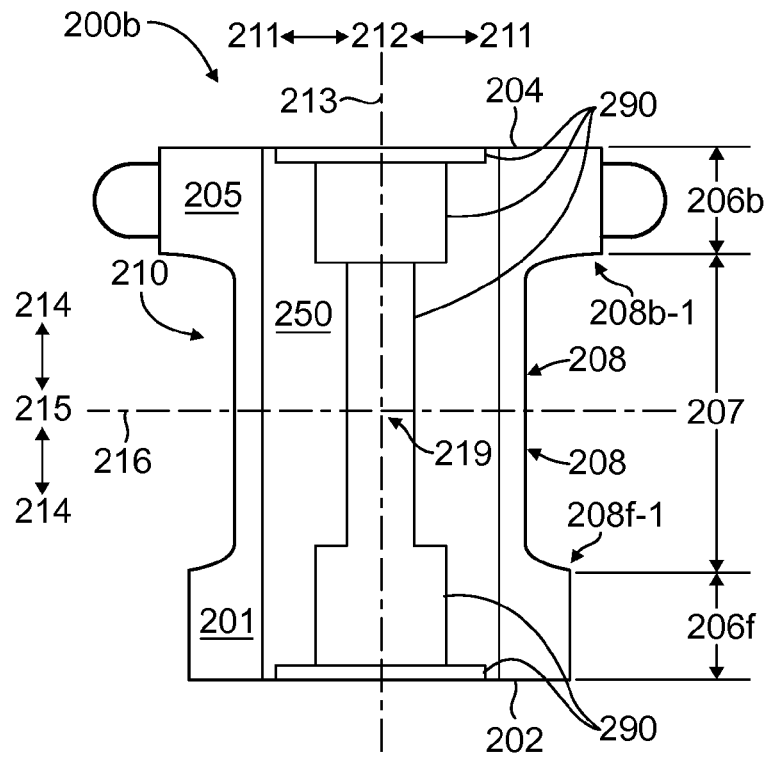
FIG. 2B illustrates a top view of an inside of a front-fastenable wearable absorbent article laid out in a flat and uncontracted state, including an absorbent core assembly joined to a stretchable outer cover, according to embodiments of the present disclosure.

FIG. 2B illustrates a top view of an inside of a front-fastenable wearable absorbent article 200B laid out in a flat and uncontracted state, including an absorbent core assembly 250 joined to a stretchable outer cover 210, according to embodiments of the present disclosure. The wearable absorbent article 200C includes a front 201, a front waist edge 202, a back waist edge 204, a back 205, a front hip region 206F, a back hip region 206B, a crotch region 207, and a leg opening edge 208.

In the wearable absorbent article 200B, the leg opening edge 208 is clearly defined and cut-to-shape. The wearable absorbent article 200B includes a farthest back longitudinally outboard point 208B-1 along the leg opening edge 208 and in the back 205. Thus, the back hip region 206B can have an overall longitudinal length measured longitudinally from the farthest longitudinally outboard point on the adjacent waist edge 204 to the farthest back longitudinally outboard point 208B-1 of the leg opening edge 208. The wearable absorbent article 200B also includes a farthest forward longitudinally outboard point 208F-1 along the leg opening edge 208 and in the front 201. Thus, the front hip region 206F can have an overall longitudinal length measured longitudinally from the farthest longitudinally outboard point on the adjacent waist edge 202 to the farthest forward longitudinally outboard point 208F-1 of the leg opening edge 208. Alternatively, either or both of the hip regions 206B and 206F can have an overall longitudinal length that is a particular percentage of the pitch of the article, as described above.

The wearable absorbent article 200C also includes a longitudinal centerline 213 and a lateral centerline 216 defining directions for laterally outboard 211, laterally inboard 212, longitudinally outboard 214, and longitudinally inboard 215, as well as a center 219. The outer cover 210, the absorbent core assembly 250, and the attachment areas 290 in FIG. 2B can each be configured as described in connection with the embodiment of FIG. 3A. In various embodiments of the wearable absorbent article 200B, the front 201, or the back 205, or the front 201 and the back 205, can be configured as described in FIG. 3A.

Figure 2C:
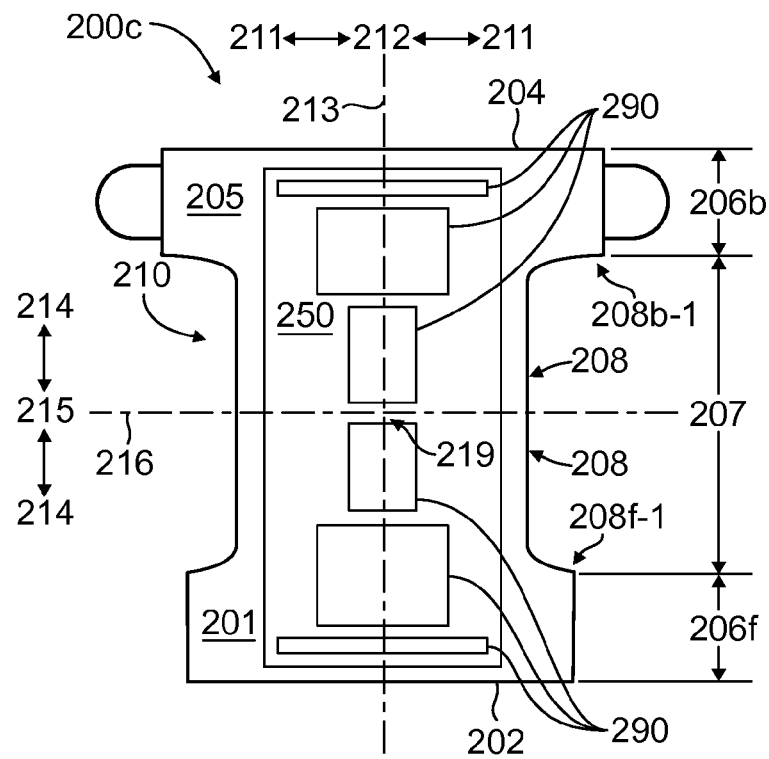
FIG. 2C illustrates a top view of an inside of a front-fastenable wearable absorbent article laid out in a flat and uncontracted state, including an absorbent core assembly joined to a stretchable outer cover, according to embodiments of the present disclosure.

FIG. 2C illustrates a top view of an inside of a front-fastenable wearable absorbent article 200C laid out in a flat and uncontracted state, including an absorbent core assembly 250 joined to a stretchable outer cover 210, according to embodiments of the present disclosure. The wearable absorbent article 200C includes a front 201, a front waist edge 202, a back waist edge 204, a back 205, a front hip region 206F, a back hip region 206B, a crotch region 207, and a leg opening edge 208. The wearable absorbent article 200C also includes a longitudinal centerline 213 and a lateral centerline 216 defining directions for laterally outboard 211, laterally inboard 212, longitudinally outboard 214, and longitudinally inboard 215, as well as a center 219. The outer cover 210, the absorbent core assembly 250, and the attachment areas 290 in FIG. 2C can each be configured as described in connection with the embodiment of FIG. 4. In various embodiments of the wearable absorbent article 200C, the front 201, or the back 205, or the front 201 and the back 205, can be configured as described in FIG. 4.

Figure 2D:
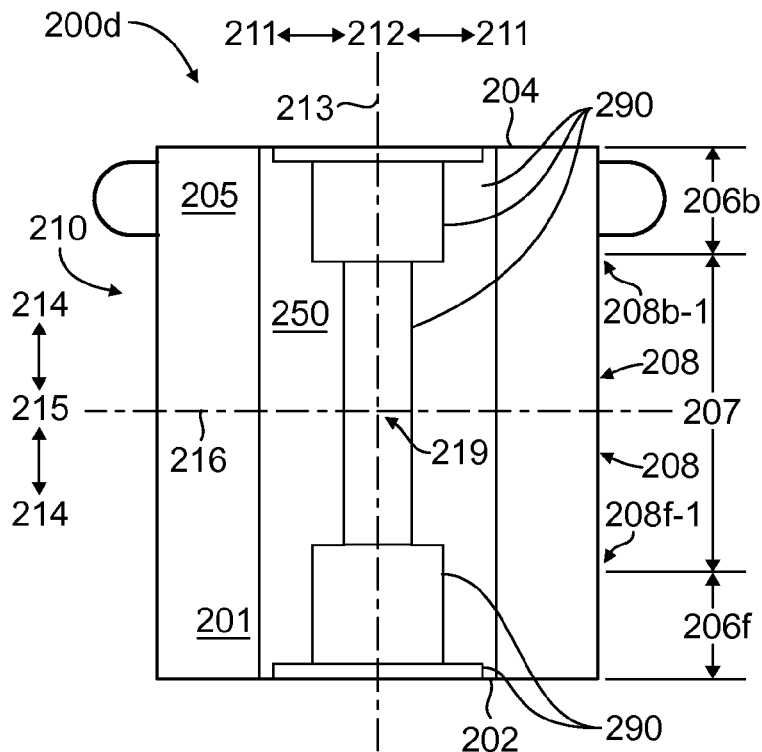
FIG. 2D illustrates a top view of an inside of a front-fastenable wearable absorbent article laid out in a flat and uncontracted state, including an absorbent core assembly joined to a stretchable outer cover, according to embodiments of the present disclosure.

FIG. 2D illustrates a top view of an inside of a front-fastenable wearable absorbent article 200D laid out in a flat and uncontracted state, according to embodiments of the present disclosure. Wearable absorbent article 200D is configured in the same way as wearable absorbent article 200B, except that, in the wearable absorbent article 200D, the leg opening edge 208 is a portion of a linear longitudinal edge, such that the wearable absorbent article 200A has an overall shape that is substantially rectangular.

Figure 2E:
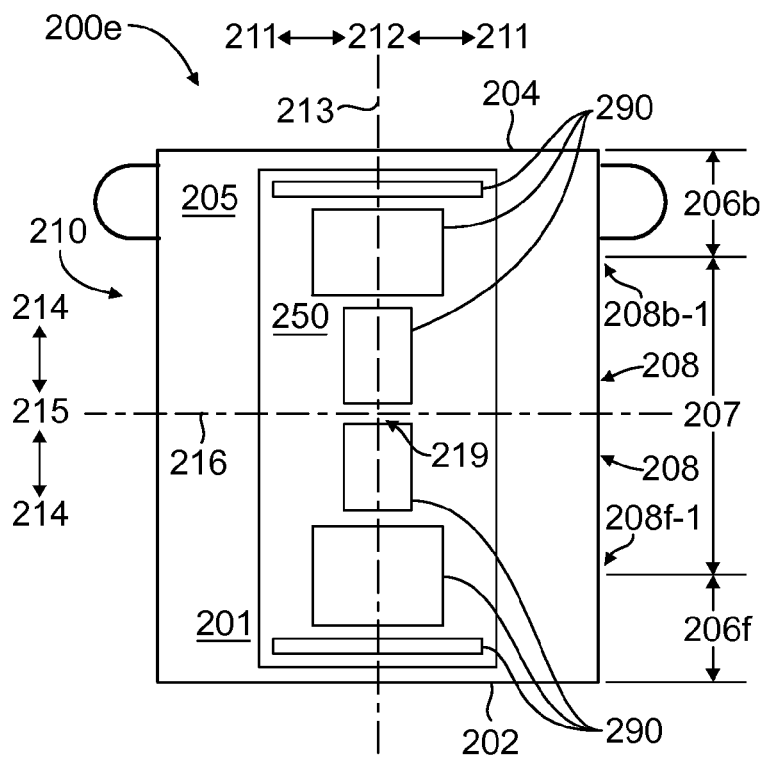
FIG. 2E illustrates a top view of an inside of a front-fastenable wearable absorbent article laid out in a flat and uncontracted state, including an absorbent core assembly joined to a stretchable outer cover, according to embodiments of the present disclosure.

FIG. 2E illustrates a top view of an inside of a front-fastenable wearable absorbent article 200E laid out in a flat and uncontracted state, according to embodiments of the present disclosure. Wearable absorbent article 200E is configured in the same way as wearable absorbent article 200C, except that, in the wearable absorbent article 200E, the leg opening edge 208 is a portion of a linear longitudinal edge, such that the wearable absorbent article 200A has an overall shape that is substantially rectangular.

Figure 3A:
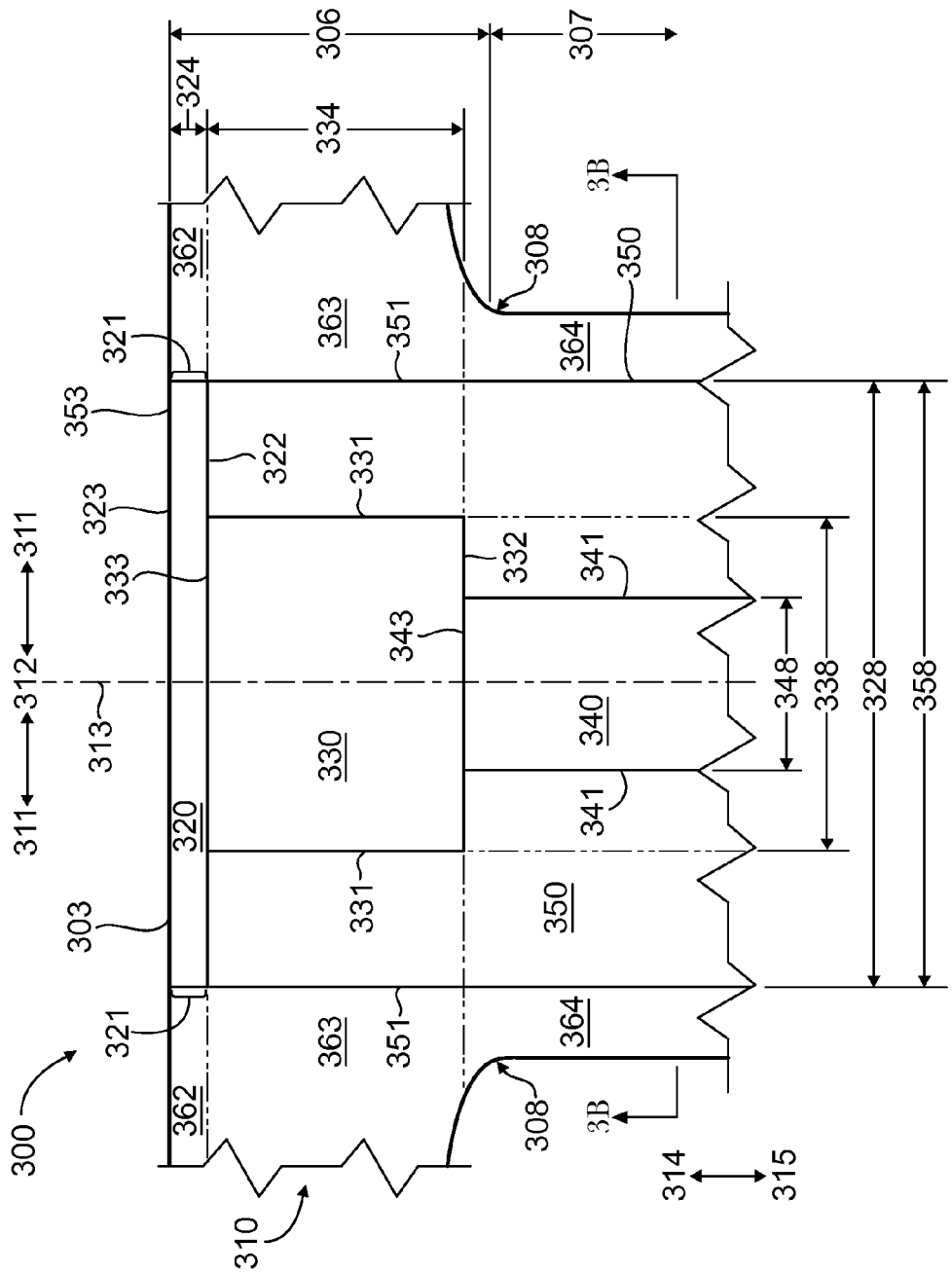
FIG. 3A illustrates a top view of an inside of a portion of a wearable absorbent article laid out in a flat and uncontracted state, including an absorbent core assembly joined to a stretchable outer cover, with a number of attachment areas, according to embodiments of the present disclosure.

FIG. 3A illustrates a top view of an inside of a portion of a wearable absorbent article 300 laid out in a flat and uncontracted state, including an absorbent core assembly 350 joined to a stretchable outer cover 310, over a first attachment area 320, a second attachment area 330, and a third attachment area 340, according to embodiments of the present disclosure. The absorbent core assembly 350 is superjacent to the attachment areas 320, 330, and 340, which are each superjacent to the stretchable outer cover 310.

For clarity, the absorbent core assembly 350 is illustrated as transparent, with visible outside edges, to better show the attachment areas 320, 330, and 340. The wearable absorbent article 300 can be a pant-type wearable absorbent article or a front-fastenable wearable absorbent article. The portion of the wearable absorbent article 300 can be a front portion or a back portion. In FIG. 3A, some outside edges of the portion are broken lines, since the portion is illustrated as separate from the rest of the wearable absorbent article 300.

The wearable absorbent article 300 includes a waist edge 303, a hip region 306, a crotch region 307, and a leg opening edge 308. The wearable absorbent article 300 also includes a longitudinal centerline 313 defining directions for laterally outboard 311 and laterally inboard 312 and also includes directions for longitudinally outboard 314 and longitudinally inboard 315.

At least a portion of the stretchable outer cover 310 is laterally stretchable, as described below. In various embodiments, part, or parts, or substantially all, or all of the stretchable outer cover 310 can be configured to be elastic or extensible, in the lateral direction, in the longitudinal direction, or in both the lateral and longitudinal directions.

As used herein, the term "stretchable" refers to the property of a material that elongates, without substantial rupture or breakage, by at least 50% at a load of between 0.1 and 10 N/cm in the Hysteresis Test (as described herein). Microsized rupture or breakage of a material is not considered substantial rupture or breakage. However, macro-sized ruptures through the structure (e.g. one or more large tears such as tears greater than about 5 mm in any direction, or breaking into two or more pieces, or resulting in significant structural degradation which may render the material unusable for its intended purpose) are considered substantial ruptures or breakage. A material that does not meet this definition for "stretchable" is considered "unstretchable." A stretchable material may be elastic or extensible as defined herein.

As used herein, the term "elastic" refers to the property of a material that elongates, without substantial rupture or breakage, by at least 50% at a load of between 0.1 and 10 N/cm in the Hysteresis Test. Further, upon release of the load, the elastic material has a set less than or equal to 20% as measured according to the Hysteresis Test. For example, an elastic material that has an initial length of 25 millimeters can elongate to at least 37.5 millimeters (50% elongation) and, upon removal of the force, retract to a length of 27.5 millimeters, i.e., have a set of 2.5 millimeters (10% set), when subjected to the Hysteresis Test. It is to be understood, however, that this definition of elastic does not apply to materials such as individual elastic strands that do not have the proper dimensions (e.g., not wide enough) to be properly subjected to the Hysteresis Test. Instead, such material is considered to be elastic if it can elongate by at least 50% upon application of a biasing force, and return substantially to its original length (i.e., exhibit less than 20% set) upon release of the biasing force.

As used herein, the term "extensible" refers to the property of a material that elongates, without substantial rupture or breakage, by at least 50% at a load of between 0.1 and 10 N/cm in the Hysteresis Test. Further, upon release of the load, the extensible material has a set greater than 20% as measured according to the Hysteresis Test. For example, an extensible material that has an initial length of 25 millimeters can elongate at least to 37.5 millimeters (50% elongation) and, upon removal of the applied force, retract to a length of 35 millimeters, i.e., have a set of 10 millimeters (40% set), when subjected to the Hysteresis Test.

An absorbent core assembly includes a core with one or more absorbent materials, such as wood pulp and/or superabsorbent particles, and may include one or more additional compositions, materials, or structures for receiving, containing, storing, and/or treating bodily waste, as known in the art. For example, an absorbent core assembly may comprise one or more layers such as a liquid-permeable topsheet, an acquisition layer, a distribution layer, a storage layer, and a liquid impermeable backsheet. Alternatively, a backsheet may be configured to resist transmitting liquid. A backsheet may or may not be configured to be breathable. An absorbent core assembly may also include one or more of various structures, such as barrier leg cuffs, a feces containment compartment, a spine (e.g. a central support structure, as described in published US patent application 2007-0287983A1, "Absorbent Article Having an Anchored Core Assembly"), and a wetness indicator. Further, an absorbent core assembly may include one or more of compositions such as lotions, perfumes, and sensates, on an outer surface and/or within the assembly.

The absorbent core assembly 350 includes longitudinal sides 351, a first end 353, and a second end (not shown). An absorbent core assembly has an overall lateral width measured laterally between a farthest laterally outboard point of the core assembly on one of its longitudinal sides to a farthest laterally outboard point of the core assembly on its other longitudinal side. An absorbent core assembly has an overall longitudinal length measured longitudinally between a farthest longitudinally outboard point of the core assembly on one of its ends to a farthest longitudinally outboard point of the core assembly on its other end. The absorbent core assembly 350 has a substantially uniform lateral width 358 along its entire overall longitudinal length. However, in various embodiments, an absorbent core assembly can have varying lateral widths over part, or parts, or all of its overall longitudinal length. The absorbent core assembly 350 has an overall longitudinal length equal to the overall longitudinal length of the wearable absorbent article 300. As a result, the first end 353 coincides with the waist edge 303. In some embodiments, however, an absorbent core assembly can have an overall longitudinal length that is shorter than the overall longitudinal length of the article. As a result, either end or both ends of the absorbent core assembly can be disposed longitudinally inboard to one or both waist edges of the article.

The absorbent core assembly 350 is joined to the stretchable outer cover 310, over a first attachment area 320, a second attachment area 330, and a third attachment area 340. As used herein, the term "joined" refers to configurations wherein an element is directly secured to another element and to configurations wherein an element is indirectly secured to another element by connecting the element to one or more intermediate members, which are, in turn connected to the other element. In a joined configuration, an element can be secured to another element with any kind of connection, such as the connections of the embodiments of FIGS. 5A-10B. Also, as used herein, the term "attachment area" refers to a two-dimensional location, having a defined outer boundary, over which an absorbent core assembly is effectively joined to an outer cover of a wearable absorbent article. Any or all of the first attachment area 320, the second attachment area 330, and the third attachment area 340, can be configured as described in connection with the embodiments of FIGS. 5A-10B. In some embodiments, one or more attachment areas can be used to form anchoring bands or anchoring systems as described in published US patent application 2007-0287983A1, "Absorbent Article Having an Anchored Core Assembly."

The first attachment area 320 is disposed in the hip region 306 of the wearable absorbent article 300 longitudinally outboard from the second attachment area 330. However, in some embodiments, a first attachment area may only be partially longitudinally outboard from a second attachment area. For example, in an embodiment where a second attachment area includes a farthest longitudinally outboard point, a portion of the first attachment area may be longitudinally outboard from that point while a portion of the first attachment area may be longitudinally inboard to that point, as described in connection with the embodiment of FIG. 3C. The first attachment area 320 overlaps the longitudinal centerline 313 and is laterally centered within the wearable absorbent article 300, although in various embodiments, an attachment area may not be laterally centered within a wearable absorbent article. The first attachment area 320 is disposed in the hip region 306 of the wearable absorbent article 300 longitudinally outboard from the second attachment area 330. The first attachment area 320 is adjacent to the second attachment area 330. Alternatively, a first attachment area may be spaced apart from a second attachment area, as described in connection with the embodiment of FIG. 4.

Throughout the present disclosure, each attachment area has an overall lateral width, measured laterally across the widest width of an attachment area, as described herein. When an attachment area overlaps a longitudinal centerline of the article, then the attachment area has an overall lateral width measured laterally between a farthest laterally outboard point of the area on one side of the longitudinal centerline to a farthest laterally outboard point of the area on the other side of the longitudinal centerline. If an attachment area does not overlap a longitudinal centerline of the article, then the attachment area has an overall lateral width measured laterally between a farthest laterally inboard point of the area to a farthest laterally outboard point of the area. Throughout the present disclosure, for a second attachment area, the overall lateral width is measured laterally across the widest width of the portion of the second attachment area that is disposed within the hip region of the article using points as described immediately above within the hip region and disregarding any width measurements outside of the hip region.

Throughout the present disclosure, each attachment area has an overall longitudinal length, measured longitudinally along the longest length of an attachment area. When an attachment area overlaps a lateral centerline of the article, then the attachment area has an overall longitudinal length measured longitudinally between a farthest longitudinally outboard point of the area on one side of the lateral centerline to a farthest longitudinally outboard point of the area on the other side of the lateral centerline. If an attachment area does not overlap a lateral centerline of the article, then the attachment area has an overall longitudinal length measured longitudinally between a farthest longitudinally inboard point of the area to a farthest longitudinally outboard point of the area.

The first attachment area 320 includes longitudinal sides 321, a longitudinally inboard end 322, and a longitudinally outboard end 323. The first attachment area 320 has a substantially uniform overall longitudinal length 324 and a substantially uniform overall lateral width 328. In some embodiments, an attachment area can have varying lateral widths over its overall longitudinal length. Also, in various embodiments, an attachment area can have varying longitudinal lengths over its overall lateral width.

The outer edges of the first attachment area 320 extend to the outer edges of the absorbent core assembly 350 such that the longitudinal sides 321 of the first attachment area 320 coincide with portions of the longitudinal sides 351 of the absorbent core assembly 350 and the longitudinally outboard end 323 of the first attachment area 320 coincides with the first end 353 of the absorbent core assembly 350. In various embodiments, one or more of outer edges of a first attachment area may only partially coincide with outer edges of an absorbent core assembly. Alternatively, one or more outer edges of a first attachment area may not extend to outer edges of the absorbent core assembly, as described in connection with the embodiment of FIG. 4. A portion of the longitudinally inboard end 322 of the first attachment area 320 coincides with a longitudinally outboard end 333 of the second attachment area 330.

Specific dimensions for an overall lateral width and an overall longitudinal length of a first attachment area for joining an absorbent core assembly to a stretchable outer cover in a wearable absorbent article can be selected as follows. In general, the first attachment area should be large enough to adequately hold the absorbent core assembly in place inside the outer cover, to prevent the absorbent core assembly from folding inward on itself, and to provide sufficient structural resistance to tension elastics located within the absorbent core assembly. At the same time, the first attachment area should not be so large as to unduly constrain the degree to which the outer cover can be extended. Similarly, if the first attachment area is disposed superjacent to a stretchable waistband structure, then the first attachment area should not be so large as to unduly constrain the degree to which the waistband can be extended. The use of these design principles is guided by the degree of extensibility in the outer cover and/or the waistband. Where the outer cover and/or waistband are more stretchable, a larger attachment area may be possible; however, where the outer cover and/or waistband are less stretchable, a smaller attachment area may be necessary.

In various embodiments, the overall longitudinal length of a first attachment area can be any length from 1 to 60 millimeters, any length from 5 to 40 millimeters, or any length from 10 to 20 millimeters, or any integer value for millimeters of length within any of these ranges. Alternatively, in some embodiments, the overall longitudinal length of a first attachment area can be any percentage from 1% to 15% of the overall longitudinal length of the wearable absorbent article, any percentage from 1% to 10% of the overall longitudinal length of the wearable absorbent article, or any percentage from 1% to 5% of the overall longitudinal length of the wearable absorbent article, or any integer value for percentage within any of these ranges. The overall lateral width of a first attachment area is discussed further in connection with the embodiment of FIG. 4.

The stretchable outer cover 310 includes an area subjacent to the first attachment area 320. The area of the stretchable outer cover 310 that is subjacent to the first attachment area 320 may or may not be formed from stretchable material.

The stretchable outer cover 310 also includes two areas 362, each disposed directly laterally outboard from the first attachment area 320. As used herein, the phrase "directly laterally outboard" refers to a relative disposition in a wearable absorbent article that is laterally outboard from a referenced area as well as at or within the same longitudinal location as the referenced area. The two areas 362 are at the same longitudinal location as the first attachment area 320. The longitudinal location of the first attachment area 320 is defined by the longitudinally inboard end 322 and the longitudinally outboard end 323. As a result, the longitudinal location of the areas 362 is also defined by the longitudinally inboard end 322 and the longitudinally outboard end 323 of the first attachment area 320. In FIG. 3A, a lateral reference line drawn from a farthest longitudinally inboard point on the longitudinally inboard end 322 of the first attachment area 320 marks the longitudinally inboard boundary of the areas 362. In various embodiments, an area that is directly laterally outboard from an attachment area, may be adjacent to the attachment area or may be spaced apart from the attachment area.

In the embodiment of FIG. 3A, each of the areas 362 is laterally stretchable. However, in some embodiments, only one of the areas directly laterally outboard from the first attachment area may be laterally stretchable. Either or both of the areas 362 may be laterally elastic, or laterally extensible, or a combination of laterally elastic and laterally extensible. Either or both of the areas 362 may be longitudinally stretchable or longitudinally unstretchable. In alternative embodiments, either or both of the areas 362 may be substantially or completely unstretchable.

In the embodiment of FIG. 3A, the relatively wide overall lateral width 328 of the first attachment region 320, placed in a longitudinally outboard portion of the article, can provide adequate structural support for the first end 353 of the absorbent core assembly 350, where it is particularly useful. Thus, in the wearable absorbent article 300, the absorbent core assembly 350 can be suitably joined to stretchable outer cover 310, such that the article 300 can look attractive and feel comfortable while being less likely to leak.

The entire second attachment area 330 is disposed in the hip region 306 of the wearable absorbent article 300. However, in various embodiments, a second attachment area may be disposed only partially within a hip region of a wearable absorbent article, as described in connection with the embodiment of FIG. 3C. The second attachment area 330 overlaps the longitudinal centerline 313 and is laterally centered within the wearable absorbent article 300, although in various embodiments, an attachment area may not be laterally centered within a wearable absorbent article. The entire second attachment area 330 is also disposed longitudinally inboard to the first attachment area 320 and longitudinally outboard from the third attachment area 340. However, in some embodiments, a second attachment area may be only partially longitudinally inboard to a first attachment area. For example, in an embodiment where a first attachment area includes a nearest longitudinally inboard point, a portion of the second attachment area may be longitudinally inboard to that point while a portion of the second attachment area may be longitudinally outboard from that point, as described in connection with the embodiment of FIG. 3C. Also, in some embodiments, a second attachment area may be only partially longitudinally outboard from a third attachment area. As an example, in an embodiment where a third attachment area includes a furthest longitudinally outboard point, a portion of the second attachment area may be longitudinally outboard from that point while a portion of the second attachment area may be longitudinally inboard to that point, as described in connection with the embodiment of FIG. 3C. The second attachment area 330 is adjacent to the first attachment area 320 and adjacent to the third attachment area 340. Alternatively, a second attachment area may be spaced apart from a first attachment area and/or a third attachment area, as described in connection with the embodiment of FIG. 4.

In an alternate embodiment, a wearable absorbent article can be constructed without a third attachment area. In a variation of this alternate embodiment, a second attachment area may be extended longitudinally inboard. For example, a second attachment area can be extended to or through a center of a wearable absorbent article. As a further example, a second attachment area can be extended from a first attachment area, through a center of the article, to another first attachment area in another half of a wearable absorbent article.

The second attachment area 330 includes longitudinal sides 331, a longitudinally inboard end 332, and a longitudinally outboard end 333. The second attachment area 330 has a substantially uniform overall longitudinal length 334 and a substantially uniform overall lateral width 338. However, in some embodiments, an attachment area can have varying widths and lengths.

The second attachment area 330 is narrower than the first attachment area 320. As a result, the overall lateral width 338 of the second attachment area 330 is less than the overall lateral width 328 of the first attachment area 320. However, in some embodiments, only a portion of the second attachment area 330 may have an overall lateral width that is less than the overall lateral width 328 of the first attachment area 320. For example, in an embodiment wherein a second attachment area is disposed only partially within a hip region of a wearable absorbent article, the second attachment area can be configured such that only the portion of the second attachment area that is disposed in the first hip region has an overall lateral width that is less than the overall lateral width of the first attachment area. In this example, the portion of the second attachment area that is outside of the hip region may or may nor have an overall lateral width that is less than the overall lateral width of the first attachment area.

The longitudinal sides 331 of the second attachment area 330 are disposed laterally inboard to the longitudinal sides 321 of the first attachment area 320 and laterally inboard to the longitudinal sides 351 of the absorbent core assembly 350.

A portion of the longitudinally inboard end 332 of the second attachment area 330 coincides with a longitudinally outboard end 343 of the third attachment area 340. In various embodiments, a longitudinally inboard end of a second attachment area may only partially coincide with a longitudinally outboard end of a third attachment area. For example, a longitudinally inboard end of a second attachment area and a longitudinally outboard end of a third attachment area may have a shared boundary that is shorter than the width of one or both of the ends. The longitudinally outboard end 333 of the second attachment area 330 coincides with a portion of a longitudinally inboard end 332 of the first attachment area 320. In some embodiments, a longitudinally outboard end of a second attachment area may only partially coincide with a portion of a longitudinally inboard end of a first attachment area.

Specific dimensions for an overall lateral width and an overall longitudinal length of a second attachment area for joining an absorbent core assembly to a stretchable outer cover in a wearable absorbent article can be selected as follows. In general, the second attachment area should be large enough to adequately hold the absorbent core assembly in place inside the outer cover and to prevent the absorbent core assembly from folding inward on itself. At the same time, the first attachment area should not be so large as to unduly constrain the degree to which the outer cover can be extended. The use of these design principles is guided by the degree of extensibility in the outer cover, as described above.

The overall lateral width of a second attachment area can be understood in terms of absolute dimensions and in terms of relative size. In various embodiments, the overall lateral width of a second attachment area can be any width from 5 to 110 millimeters, any width from 5 to 60 millimeters, or any width from 5 to 25 millimeters, or any integer value for millimeters of width within any of these ranges. Alternatively, in some embodiments, the overall lateral width of a second attachment area can be any percentage from 3% to 95% of the overall lateral width of the absorbent core assembly, any percentage from 3% to 90% of the overall lateral width of the absorbent core assembly, or any percentage from 3% to 50% of the overall lateral width of the absorbent core assembly, or any integer value for percentage within any of these ranges. The overall longitudinal length of a second attachment area can be any length.

The stretchable outer cover 310 includes an area subjacent to the second attachment area 330. The area of the stretchable outer cover 310 that is subjacent to the second attachment area 330 may or may not be formed from stretchable material.

The stretchable outer cover 310 also includes two areas 363, each disposed directly laterally outboard from the second attachment area 330. The two areas 363 are at the same longitudinal location as the second attachment area 330. The longitudinal location of the second attachment area 330 is defined by the longitudinally inboard end 332 and the longitudinally outboard end 333. As a result, the longitudinal location of the areas 363 is also defined by the longitudinally inboard end 332 and the longitudinally outboard end 333 of the second attachment area 330. In FIG. 3A, a lateral reference line drawn from a farthest longitudinally inboard point on the longitudinally inboard end 332 of the second attachment area 330 marks the longitudinally inboard boundary of the areas 363 and a lateral reference line drawn from a farthest longitudinally outboard point on the longitudinally outboard end 333 of the second attachment area 330 marks the longitudinally outboard boundary of the areas 363.

In the embodiment of FIG. 3A, each of the areas 363 is laterally stretchable. However, in some embodiments, only one of the areas directly laterally outboard from the second attachment area may be laterally stretchable. Either or both of the areas 363 may be laterally elastic, or laterally extensible, or a combination of laterally elastic and laterally extensible. Either or both of the areas 363 may be longitudinally stretchable or longitudinally unstretchable.

In the embodiment of FIG. 3A, the relatively narrow overall lateral width 338 of the second attachment region 330, placed in the hip region 306 of the wearable absorbent article 300, can allow a significant degree of extensibility around a large circumference of a wearer's body (e.g. the fullest part of the buttocks), where it is especially beneficial. Thus, in the wearable absorbent article 300, the absorbent core assembly 350 can be suitably joined to stretchable outer cover 310, such that the article 300 can look attractive and feel comfortable while being less likely to leak.

Substantially all of the third attachment area 340 is disposed in the crotch region 307 of the wearable absorbent article 300. However, in various embodiments, all of a third attachment area may be disposed within a crotch region of a wearable absorbent article. The third attachment area 340 overlaps the longitudinal centerline 313 and is laterally centered within the wearable absorbent article 300, although in various embodiments, an attachment area may not be laterally centered within a wearable absorbent article. The entire third attachment area 340 is disposed longitudinally inboard to the second attachment area 330. However, in some embodiments, a third attachment area may be only partially longitudinally inboard to a second attachment area. For example, in an embodiment where a second attachment area includes a nearest longitudinally inboard point, a portion of the third attachment area may be longitudinally inboard to that point while a portion of the third attachment area may be longitudinally outboard from that point, as described in connection with the embodiment of FIG. 3C. The third attachment area 340 is adjacent to the second attachment area 330. Alternatively, a third attachment area may be spaced apart from a second attachment area, as described in connection with the embodiment of FIG. 4.

The third attachment area 340 includes longitudinal sides 341, a first end 343, and a second end (not shown). A third attachment area can extend to or through a center of a wearable absorbent article. In some embodiments, a third attachment area can extend through a center of a wearable absorbent article, to another second attachment area in the other half of the article.

The third attachment area 340 has a substantially uniform overall lateral width 348. However, in some embodiments, an attachment area can have varying widths. The overall lateral width of a third attachment area differs from an overall lateral width of a second attachment area. In the embodiment of FIG. 3A, the overall lateral width 348 of the third attachment area 340 is less than the overall lateral width 338 of the second attachment area 330. The longitudinal sides 341 of the third attachment area 340 are disposed laterally inboard to the longitudinal sides 331 of the second attachment area 330 and laterally inboard to the longitudinal sides 351 of the absorbent core assembly 350. However, in alternate embodiments, an overall lateral width of a third attachment area can be equal to or greater than an overall lateral width of a second attachment area. Further, in additional alternate embodiments, an overall lateral width of a third attachment area can be less than, equal to, or greater than an overall lateral width of a first attachment area.

The first end 343 of the third attachment area 340 coincides with a portion of the longitudinally inboard end 332 of the second attachment area 330. In various embodiments, an end of a third attachment area may only partially coincide with a longitudinally inboard end of a second attachment area.

Specific dimensions for an overall lateral width and an overall longitudinal length of a third attachment area for joining an absorbent core assembly to a stretchable outer cover in a wearable absorbent article can be selected as follows. In general, the third attachment area should be large enough to adequately hold the absorbent core assembly in place inside the outer cover and should be small enough so as not to inhibit leg cuff contractions in the absorbent core assembly and/or in contracted portions along the longitudinal sides of the article. In various embodiments, a third attachment area can have an overall lateral width that is greater than or equal to 3%, or 5%, or 10% (or any integer value between any of these percentages) of the overall lateral width of the absorbent core assembly of the wearable absorbent article. In some embodiments, a third attachment area can have an overall lateral width that is less than or equal to 100%, or 90%, or 70% (or any integer value between any of these percentages) of the overall lateral width of the absorbent core assembly of the wearable absorbent article.

The stretchable outer cover 310 includes an area subjacent to the third attachment area 340. The area of the stretchable outer cover 310 that is subjacent to the third attachment area 340 may or may not be formed from stretchable material.

The stretchable outer cover 310 also includes two areas 364, each disposed directly laterally outboard from the third attachment area 340. The two areas 364 are at the same longitudinal location as the third attachment area 340. The longitudinal location of the third attachment area 340 is defined by the first end 343 and the second end (not shown). As a result, the longitudinal location of the areas 364 is also defined by the first end 343 and the second end of the second attachment area 340. In FIG. 3A, a lateral reference line drawn from a farthest longitudinally outboard point on the first end 343 of the third attachment area 340 marks one of the boundaries of the areas 363. The opposing boundary for the area 363 is not shown in FIG. 3A.

In the embodiment of FIG. 3A, each of the areas 364 is laterally stretchable. However, in some embodiments, only one of the areas directly laterally outboard from the second attachment area may be laterally stretchable. Either or both of the areas 364 may be laterally elastic, or laterally extensible, or a combination of laterally elastic and laterally extensible. Either or both of the areas 364 may be longitudinally stretchable or longitudinally unstretchable.

In the embodiment of FIG. 3A, the third attachment region 340 of the wearable absorbent article 300, can adequately hold the absorbent core assembly 350 in place inside the stretchable outer cover 310, in the crotch region 307. Thus, in the wearable absorbent article 300, the absorbent core assembly 350 can be suitably joined to stretchable outer cover 310, such that the article 300 can look attractive and feel comfortable while being less likely to leak.

Figure 3B:
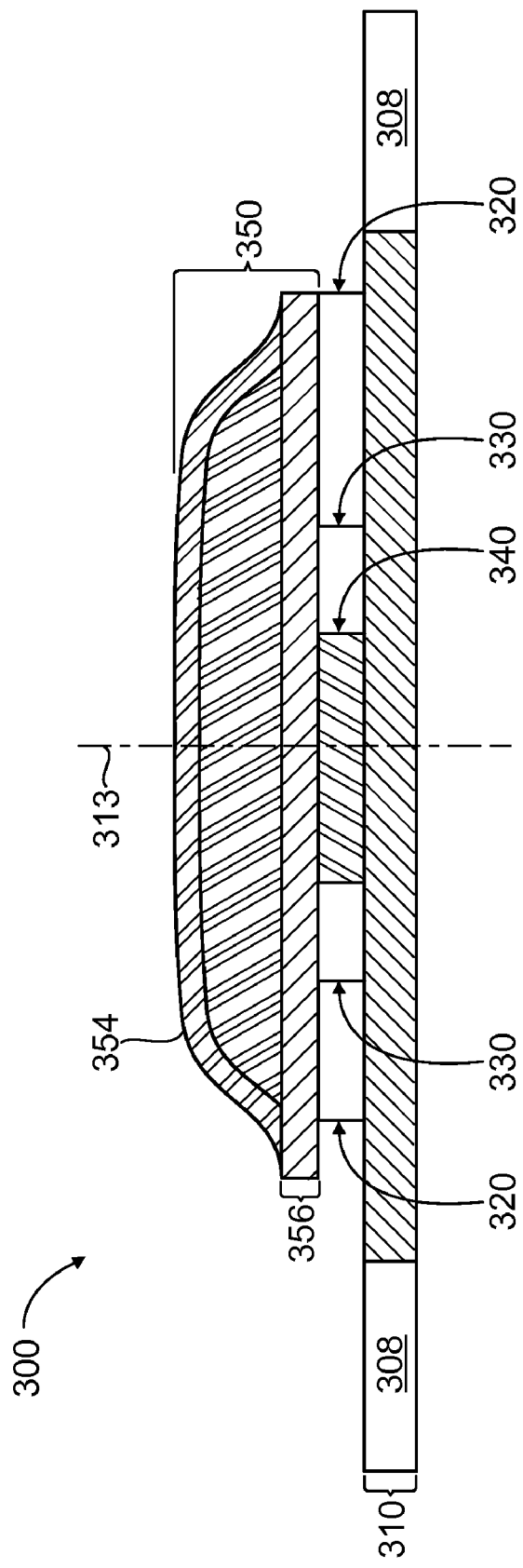
FIG. 3B illustrates a cross-sectional side view of the portion of the wearable absorbent article of the embodiment of FIG. 3A.

FIG. 3B illustrates a cross-sectional side view of the portion of the wearable absorbent article 300 of the embodiment of FIG. 3A. The wearable absorbent article 300 includes the absorbent core assembly 350 joined to the stretchable outer cover 310, over the first attachment area 320, the second attachment area 330, and the third attachment area 340. FIG. 3B also illustrates the leg opening edge 308 and an orthogonal projection of the longitudinal centerline 313. In the embodiment of FIG. 3B, the absorbent core assembly 350 includes a liquid permeable layer 354 forming the top surface of the absorbent core assembly 350, a liquid impermeable layer 356 forming the back surface of the absorbent core assembly 350, and absorbent material 355 disposed in between the liquid permeable layer 354 and the liquid impermeable layer 356.

In the embodiment of FIG. 3B, each of the attachment areas 320, 330, and 340 directly connects the absorbent core assembly 350 to the stretchable outer cover 310, although direct connections are not required. In alternative embodiments, one or more of the attachment areas 320, 330, and 340 can indirectly connect the absorbent core assembly 350 to the stretchable outer cover 310. Each of the attachment areas 320, 330, and 340 has the same overall uniform thickness, although in various embodiments, the thickness can vary within an attachment area, and/or from one attachment area to another. Any or all of the first attachment area 320, the second attachment area 330, and the third attachment area 340, can be configured as described in connection with the embodiments of FIGS. 5A-10B.

Figure 3C:
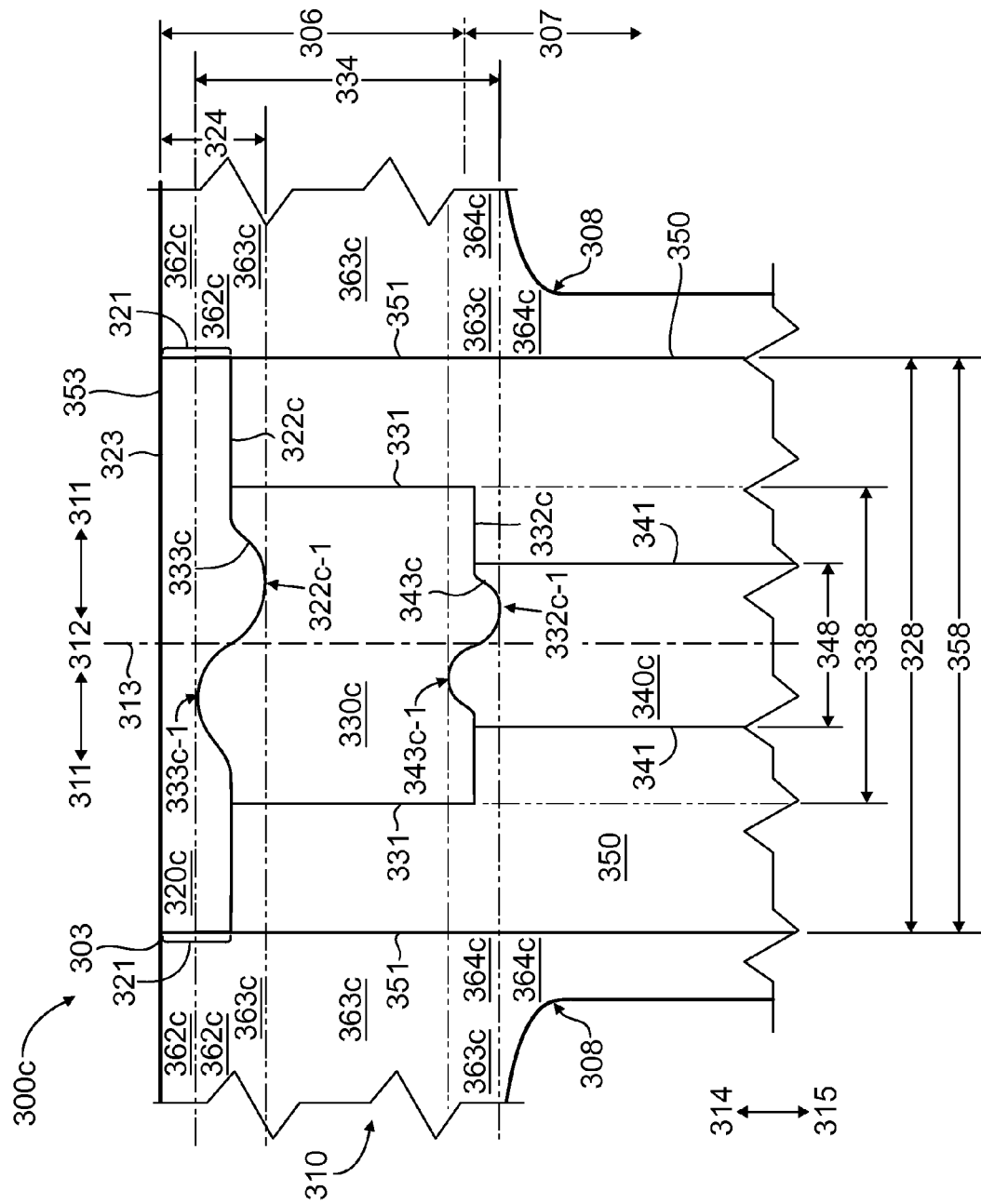
FIG. 3C illustrates a top view of an inside of a portion of a wearable absorbent article laid out in a flat and uncontracted state, including an absorbent core assembly joined to a stretchable outer cover, with a number of attachment areas, according to embodiments of the present disclosure.

FIG. 3C illustrates a top view of an inside of a portion of a wearable absorbent article 300C laid out in a flat and uncontracted state. Each of the elements of the embodiment of FIG. 3C is configured in the same way as the like-numbered element of the embodiment of FIG. 3A, except as described below. Throughout the present disclosure, the term "like-numbered" is intended to indicate a correspondence between labels of elements wherein the last two numbers in the labels of the elements are the same. Element labels are considered to be like-numbered despite differing numeral prefixes corresponding to figure numbers, and despite differing suffixes corresponding to particular embodiments. The wearable absorbent article 300C includes the absorbent core assembly 350 joined to the stretchable outer cover 310, over a first attachment area 320C, a second attachment area 330C, and a third attachment area 340C.

The first attachment area 320C includes a longitudinally inboard end 322C with a farthest longitudinally inboard point 322C-1. The first attachment area 320C has varying longitudinal lengths over its overall lateral width. A portion of the longitudinally inboard end 322C of the first attachment area 320C coincides with a longitudinally outboard end 333C of the second attachment area 330C. The longitudinally outboard end 333C includes a farthest longitudinally outboard point 333C-1. Since the farthest longitudinally inboard point 322C-1 is longitudinally inboard to the farthest longitudinally outboard point 333C-1, the first attachment area 320C is only partially longitudinally outboard from the second attachment area 330C. As a result, areas 362C and 363C partially overlap.

Substantially all of the second attachment area 330C is disposed in the hip region 306 of the wearable absorbent article 300C. The second attachment area 330C includes a longitudinally inboard end 332C with a farthest longitudinally inboard point 332C-1. The second attachment area 330C has varying longitudinal lengths over its overall lateral width. A portion of the longitudinally inboard end 332C of the second attachment area 330C coincides with a first end 343C of the third attachment area 340C. The first end 343C includes a farthest longitudinally outboard point 343C-1. Since the farthest longitudinally inboard point 332C-1 is longitudinally inboard to the farthest longitudinally outboard point 343C-1, the second attachment area 330C is only partially longitudinally outboard from the third attachment area 340C. As a result, areas 363C and 364C partially overlap.

Figure 4:
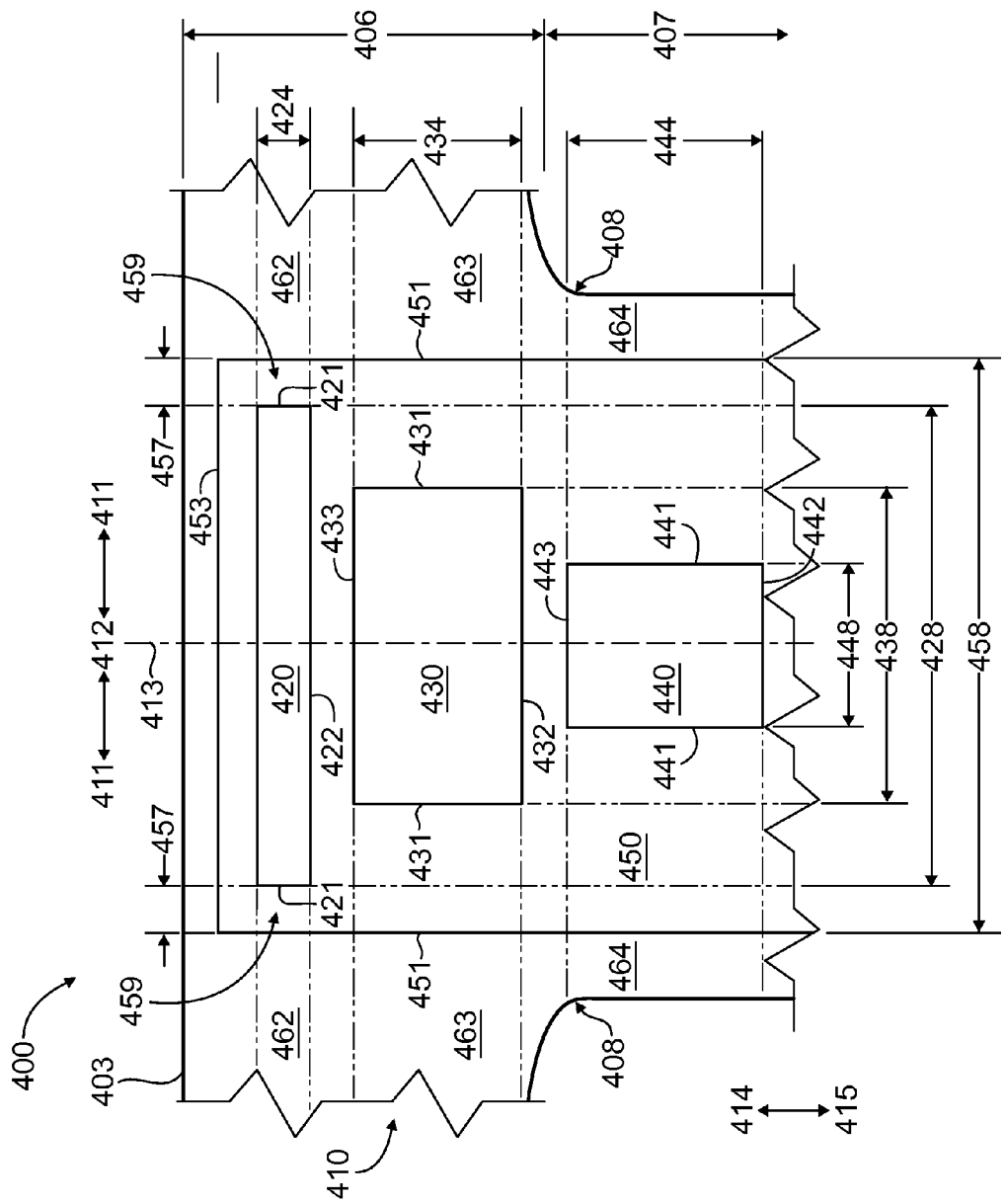
FIG. 4 illustrates a top view of an inside of another portion of a wearable absorbent article laid out in a flat and uncontracted state, including an absorbent core assembly joined to a stretchable outer cover, with a number of attachment areas, according to embodiments of the present disclosure.

FIG. 4 illustrates a top view of an inside of another portion of a wearable absorbent article 400 laid out in a flat and uncontracted state, including an absorbent core assembly 450 joined to a stretchable outer cover 410, over a first attachment area 420, a second attachment area 430, and a third attachment area 440, according to embodiments of the present disclosure. The absorbent core assembly 450 is superjacent to the attachment areas 420, 430, and 440, which are each superjacent to the stretchable outer cover 310.

For clarity, the absorbent core assembly 450 is illustrated as transparent, with visible outside edges, to better show the attachment areas 420, 430, and 440. The wearable absorbent article 400 can be a pant-type wearable absorbent article or a front-fastenable wearable absorbent article. The portion of the wearable absorbent article 400 can be a front portion or a back portion. In FIG. 4, some outside edges of the portion are broken lines, since the portion is illustrated as separate from the rest of the wearable absorbent article 400.

The wearable absorbent article 400 includes a waist edge 403, a hip region 406, a crotch region 407, and a leg opening edge 408. The wearable absorbent article 400 also includes a longitudinal centerline 413 defining directions for laterally outboard 411 and laterally inboard 412 and also includes directions for longitudinally outboard 414 and longitudinally inboard 415.

At least a portion of the stretchable outer cover 410 is laterally stretchable, as described below. In various embodiments, part, or parts, or substantially all, or all of the stretchable outer cover 410 can be configured to be elastic or extensible, in the lateral direction, in the longitudinal direction, or in both the lateral and longitudinal directions.

The absorbent core assembly 450 includes longitudinal sides 451, a first end 453, and a second end (not shown). The absorbent core assembly 450 has a substantially uniform width 458 along its entire overall longitudinal length. The absorbent core assembly 450 has an overall longitudinal length that is shorter than the overall longitudinal length of the article 400. As a result, the first end 453 is disposed longitudinally inboard to the waist edge 403. In some embodiments, however, an absorbent core assembly can have an overall longitudinal length that is equal to the overall longitudinal length of the article. As a result, either end or both ends of the absorbent core assembly can coincide with one or both waist edges of the article.

The absorbent core assembly 450 is joined to the stretchable outer cover 410, over a first attachment area 420, a second attachment area 430, and a third attachment area 440. Any or all of the first attachment area 420, the second attachment area 430, and the third attachment area 440, can be configured as described in connection with the embodiments of FIGS. 5A-10B.

The first attachment area 420 is disposed in the hip region 406 of the wearable absorbent article 400, longitudinally outboard from the second attachment area 430. The first attachment area 420 overlaps the longitudinal centerline 413 and is laterally centered within the wearable absorbent article 400. The first attachment area 420 is spaced apart from the second attachment area 430. Alternatively, a first attachment area may be adjacent to a second attachment area, as described in connection with the embodiment of FIG. 3A.

The first attachment area 420 includes longitudinal sides 421, a longitudinally inboard end 422, and a longitudinally outboard end 423. The first attachment area 420 has a substantially uniform overall longitudinal length 424 and a substantially uniform overall lateral width 428.

The longitudinal sides 421 of the first attachment area 420 are disposed laterally inboard to the longitudinal sides 451 of the absorbent core assembly 450. As a result, the absorbent core assembly 450 includes two unattached areas 459, each disposed directly laterally outboard from the first attachment area 420. The absorbent core assembly 450 is not joined to the stretchable outer cover 410 over the unattached areas 459.

Each of the unattached areas 459 is bounded on a laterally outboard side by a longitudinal side 451 of the absorbent core assembly 450, on a laterally inboard side by a longitudinal side 421 of the first attachment area 420, on a longitudinally outboard side by an imaginary line extending laterally from the longitudinally outboard end 423 of the first attachment area 420, and on a longitudinally inboard side by an imaginary line extending laterally from the longitudinally inboard end 422 of the first attachment area 420. Each of the unattached areas 459 has a lateral width 457 measured laterally between the longitudinal side 451 of the absorbent core assembly 450 and the longitudinal side 421 of the first attachment area 420. Also, each of the unattached areas 459 has a longitudinal length equal to the overall longitudinal length 424 of the first attachment area.

The lateral width of an unattached area can be understood in terms of absolute dimensions and in terms of relative size. In various embodiments, the lateral width of an unattached area can be any width from 1 to 30 millimeters, any width from 1 to 20 millimeters, any width from 1 to 10 millimeters, any width from 1 to 5 millimeters, or any integer value for millimeters of width within any of these ranges. In some embodiments, the lateral width of an unattached area can be at least 3 millimeters or at least 5 millimeters, but less than 20 millimeters. Alternatively, in some embodiments, the lateral width of an unattached area can be any percentage from 1% to 20% of the overall lateral width of the absorbent core assembly, any percentage from 1% to 15% of the overall lateral width of the absorbent core assembly, any percentage from 1% to 10% of the overall lateral width of the absorbent core assembly, or any percentage from 1% to 5% of the overall lateral width of the absorbent core assembly, or any integer value for percentage within any of these ranges.

In various embodiments, either or both of the longitudinal sides of a first attachment area may extend to longitudinal sides of an absorbent core assembly such that either or both of the longitudinal sides of the first attachment area partially or completely coincide with portions of the longitudinal sides of the absorbent core assembly. The longitudinally outboard end 423 is disposed longitudinally inboard to the first end 453 of the absorbent core assembly 450. In some embodiments, a longitudinally outboard end of a first attachment area may extend to an end of an absorbent core assembly such that the longitudinally outboard end of the first attachment area partially or completely coincides with the end of the absorbent core assembly.

Specific dimensions for a first attachment area for joining an absorbent core assembly to a stretchable outer cover in a wearable absorbent article, are described in connection with the embodiment of FIG. 3A. In addition, a first attachment area that is narrower than an absorbent core assembly should be large enough to prevent any portion of the end of the absorbent core assembly from "peeking out" (i.e. extending out beyond a waist edge of a wearable absorbent article). The first attachment area 420 can have the same overall longitudinal lengths as described for the first attachment area 320.

The overall lateral width of a first attachment area can be understood in terms of absolute dimensions and in terms of relative size. In various embodiments, the overall lateral width of a first attachment area can be any width from 80 to 140 millimeters, any width from 90 to 130 millimeters, or any width from 100 to 120 millimeters, or any integer value for millimeters of width within any of these ranges. Alternatively, in some embodiments, the overall lateral width of a first attachment area can be any percentage from 70% to 100% of the overall lateral width of the absorbent core assembly, any percentage from 75% to 95% of the overall lateral width of the absorbent core assembly, or any percentage from 80% to 90% of the overall lateral width of the absorbent core assembly, or any integer value for percentage within any of these ranges.

The stretchable outer cover 410 includes an area subjacent to the first attachment area 420. The area of the stretchable outer cover 410 that is subjacent to the first attachment area 420 may or may not be formed from stretchable material. The stretchable outer cover 410 also includes two areas 462, each disposed directly laterally outboard from the first attachment area 420. The areas 462 are configured in the same way as the areas 362, described in connection with the embodiment of FIG. 3A.

In the embodiment of FIG. 4, the relatively wide overall lateral width 428 of the first attachment region 420, placed in a longitudinally outboard portion of the article, can provide adequate structural support for the first end 453 of the absorbent core assembly 450, where it is particularly useful. Thus, in the wearable absorbent article 400, the absorbent core assembly 450 can be suitably joined to stretchable outer cover 410, such that the article 400 can look attractive and feel comfortable while being less likely to leak.

The entire second attachment area 430 is disposed in the hip region 406 of the wearable absorbent article 400. The first attachment area 420 overlaps the longitudinal centerline 413 and is laterally centered within the wearable absorbent article 400. The entire second attachment area 430 is also disposed longitudinally inboard to the first attachment area 420 and longitudinally outboard from the third attachment area 440. The second attachment area 430 is spaced apart from the first attachment area 420 and spaced apart from the third attachment area 430. Alternatively, a second attachment area may be adjacent to a first attachment area and/or a third attachment area, as described in connection with the embodiment of FIG. 3A.

The second attachment area 430 includes longitudinal sides 431, a longitudinally inboard end 432, and a longitudinally outboard end 433. The second attachment area 430 has a substantially uniform overall longitudinal length 434 and a substantially uniform overall lateral width 438.

The second attachment area 430 is narrower than the first attachment area 420. As a result, the overall lateral width 438 of the second attachment area 430 is less than the overall lateral width 428 of the first attachment area 420. The longitudinal sides 431 of the second attachment area 430 are disposed laterally inboard to the longitudinal sides 421 of the first attachment area 420 and laterally inboard to the longitudinal sides 451 of the absorbent core assembly 450. Specific dimensions for a second attachment area for joining an absorbent core assembly to a stretchable outer cover in a wearable absorbent article can be selected as described in connection with the embodiment of FIG. 3A. The second attachment area 430 can have the same overall longitudinal lengths and overall lateral widths as described for the second attachment area 330.

The stretchable outer cover 410 includes an area subjacent to the second attachment area 430. The area of the stretchable outer cover 410 that is subjacent to the second attachment area 430 may or may not be formed from stretchable material. The stretchable outer cover 410 also includes two areas 463, each disposed directly laterally outboard from the second attachment area 430. The two areas 463 are configured in the same way as the areas 363, described in connection with the embodiment of FIG. 3A.

In the embodiment of FIG. 4, the relatively narrow overall lateral width 438 of the second attachment region 430, placed in the hip region 406 of the wearable absorbent article 400, can allow a significant degree of extensibility around a large circumference of a wearer's body (e.g. the fullest part of the buttocks), where it is especially beneficial. Thus, in the wearable absorbent article 400, the absorbent core assembly 450 can be suitably joined to stretchable outer cover 410, such that the article 400 can look attractive and feel comfortable while being less likely to leak.

Substantially all of the third attachment area 440 is disposed in the crotch region 407 of the wearable absorbent article 400. The third attachment area 440 overlaps the longitudinal centerline 413 and is laterally centered within the wearable absorbent article 400. The entire third attachment area 440 is disposed longitudinally inboard to the second attachment area 430. The third attachment area 440 is spaced apart from the second attachment area 430. Alternatively, a third attachment area may be adjacent to a second attachment area, as described in connection with the embodiment of FIG. 3A.

The third attachment area 440 includes longitudinal sides 441, a longitudinally inboard end 442, and a longitudinally outboard end 443. The third attachment area 440 has a substantially uniform overall lateral width 448. In the embodiment of FIG. 4, the overall lateral width 448 of the third attachment area 440 is less than the overall lateral width 438 of the second attachment area 430. The longitudinal sides 441 of the third attachment area 440 are disposed laterally inboard to the longitudinal sides 431 of the second attachment area 430 and laterally inboard to the longitudinal sides 451 of the absorbent core assembly 450.

Specific dimensions for a third attachment area for joining an absorbent core assembly to a stretchable outer cover in a wearable absorbent article can be selected as described in connection with the embodiment of FIG. 3A.

The stretchable outer cover 410 includes an area subjacent to the third attachment area 440. The area of the stretchable outer cover 410 that is subjacent to the third attachment area 440 may or may not be formed from stretchable material. The stretchable outer cover 410 also includes two areas 464, each disposed directly laterally outboard from the third attachment area 440. The two areas 464 are configured in the same way as the areas 364, described in connection with the embodiment of FIG. 3A.

In the embodiment of FIG. 4, the third attachment region 440 of the wearable absorbent article 400 can adequately hold the absorbent core assembly 450 in place inside the stretchable outer cover 410, in the crotch region 407. Thus, in the wearable absorbent article 400, the absorbent core assembly 450 can be suitably joined to stretchable outer cover 410, such that the article 400 can look attractive and feel comfortable while being less likely to leak.

The embodiments of FIGS. 5A-10B describe and illustrate various exemplary attachment areas for joining an absorbent core assembly to an outer cover of a wearable absorbent article. For clarity, each of FIGS. 5A-10B illustrate a portion of an outer cover and a portion of an absorbent core assembly, separate from the rest of a wearable absorbent article. Also for clarity, the portions of the absorbent core assemblies are illustrated as invisible, with visible outside edges, to better show the attachment areas.

FIGS. 5A-10B illustrate attachment areas formed from one or more connections. Unless otherwise stated, each of the connections in the embodiments of FIGS. 5A-10B can any kind of connection for holding the portion of the absorbent core assembly to the portion of the outer cover. Further, each of these connections can be any number and any combination of any kind of connection. As examples, a connection can be a durable connection (such as an adhesive bond, a cohesive bond, a fusion bond, a thermal bond, or an ultrasonic bond), a frangible connection (configured to break or release when subjected to particular forces), a refastenable connection (configured to be used multiple times), a microfastener connection (such as a hook-and-loop fastening system), a macrofastener connection (such as a snap, button, or tab-and-slot), or connecting structures (such as buckles, straps, or zippers), and the like, as will be understood by one of ordinary skill in the art.

Still further, while each of the connections of FIGS. 5A-10B is a direct connection, each embodiment can be modified with the additional layers, structures, and/or other connections, to form indirect connections, which can also be used for joining an absorbent core assembly to an outer cover of a wearable absorbent article in embodiments of the present disclosure, as will be understood by one of ordinary skill in the art.

FIG. 5A illustrates a portion of a wearable absorbent article 570 with a portion of an absorbent core assembly 575 joined to a portion of a stretchable outer cover 571 over an attachment area 594, according to embodiments of the present disclosure. The attachment area 594 is a single filled square shaped connection 592, directly connecting the portion of the absorbent core assembly 575 to the portion of the stretchable outer cover 571, in a substantially continuous manner, over the attachment area 594. An outer boundary of the attachment area 594 is defined by the outer extent of the connection 592. FIG. 5B illustrates a cross-sectional view of the embodiment of FIG. 5A.

FIG. 6A illustrates a portion of a wearable absorbent article 670 with a portion of an absorbent core assembly 675 joined to a portion of a stretchable outer cover 671 over an attachment area 694, according to embodiments of the present disclosure. The attachment area 694 is formed by a one-dimensional array of multiple rectangular stripes of connections 692, directly connecting the portion of the absorbent core assembly 675 to the portion of the stretchable outer cover 671, in a regular but discontinuous manner, over the attachment area 694. The connections 692 are separated by unattached portions 693 of the attachment area 694. Despite the unattached portions 693, the portion of the absorbent core assembly 675 is considered joined to the portion of a stretchable outer cover 671 over the entire attachment area 694, because the portion of the stretchable outer cover 671 is effectively constrained from relative movement with respect to the portion of the absorbent core assembly 675, over the entire attachment area 694. In FIG. 6A, the attachment area 694 is defined by the outer sides of the outermost stripes of connections 692 and the ends of the stripes of connections 692. An outer boundary of the attachment area 694 is illustrated with dashed lines. While the multiple rectangular stripes of connections 692 are illustrated as evenly spaced apart in FIG. 6A, such even spacing is not required. Further, any of the connections 692 can have various shapes. For example, part, or parts, or all of a connection 692 can be straight, curved, angled, segmented, or another shape, or combinations of any of these shapes. FIG. 6B illustrates a cross-sectional view of the embodiment of FIG. 6A.

FIG. 7A illustrates a portion of a wearable absorbent article 770 with a portion of an absorbent core assembly 775 joined to a portion of a stretchable outer cover 771 over an attachment area 794, according to embodiments of the present disclosure. The attachment area 794 is formed by a two-dimensional array of multiple round connections 792, directly connecting the portion of the absorbent core assembly 775 to the portion of the stretchable outer cover 771, in a regular but discontinuous manner, over the attachment area 794. The connections 792 are separated by unattached portions 793 of the attachment area 794. Despite the unattached portions 793, the portion of the absorbent core assembly 775 is considered joined to the portion of a stretchable outer cover 771 over the entire attachment area 794, because the portion of the stretchable outer cover 771 is effectively constrained from relative movement with respect to the portion of the absorbent core assembly 775, over the entire attachment area 794. In FIG. 7A, the attachment area 794 is defined by tangent points on the outer sides of the outermost connections 792. An outer boundary of the attachment area 794 is illustrated with dashed lines. While the multiple round connections 792 are illustrated as evenly spaced apart in FIG. 7A, such even spacing is not required. Further, any of the connections 792 can have various shapes. For example, a connection 792 can have an overall shape that is similar to or the same as a circle, oval, ellipse, triangle, square, polygon, star, or another shape, or combinations of any of these shapes. FIG. 7B illustrates a cross-sectional view of the embodiment of FIG. 7A.

FIG. 8A illustrates a portion of a wearable absorbent article 870 with a portion of an absorbent core assembly 875 joined to a portion of a stretchable outer cover 871 over an attachment area 894, according to embodiments of the present disclosure. The attachment area 894 is formed by a single hollow square shaped connection 892, directly connecting the portion of the absorbent core assembly 875 to the portion of the stretchable outer cover 871, in a regular but discontinuous manner, over the attachment area 894. The connection 892 is considered hollow because of an unattached portion 893 in the center of the connection 892. Despite the unattached portion 893, the portion of the absorbent core assembly 875 is considered joined to the portion of a stretchable outer cover 871 over the entire attachment area 894, because the portion of the stretchable outer cover 871 is effectively constrained from relative movement with respect to the portion of the absorbent core assembly 875, over the entire attachment area 894. In FIG. 8A, the attachment area 894 is defined by the outer extent of the connection 892. While the connection 892 is illustrated as a square with four linear sides, the connection 892 can have various shapes. For example, part, or parts, or all of one or more or the sides of a connection 892 can be straight, curved, angled, segmented, or another shape, or combinations of any of these shapes. Also as an example, a connection 892 can have an overall shape that is similar to or the same as a circle, oval, ellipse, triangle, square, polygon, star, or another shape, or combinations of any of these shapes. FIG. 8B illustrates a cross-sectional view of the embodiment of FIG. 8A.

FIG. 9A illustrates a portion of a wearable absorbent article 970 with a portion of an absorbent core assembly 975 joined to a portion of a stretchable outer cover 971 over an attachment area 994, according to embodiments of the present disclosure. The attachment area 994 is formed by a two rectangular stripes of connections 992, directly connecting the portion of the absorbent core assembly 975 to the portion of the stretchable outer cover 971, in a discontinuous manner, over the attachment area 994. The connections 992 are separated by unattached portion 993 of the attachment area 994. Despite the unattached portion 993, the portion of the absorbent core assembly 975 is considered joined to the portion of a stretchable outer cover 971 over the entire attachment area 994, because the portion of the stretchable outer cover 971 is effectively constrained from relative movement with respect to the portion of the absorbent core assembly 975, over the entire attachment area 994. In FIG. 9A, the attachment area 994 is defined by the outer sides of the stripes of connections 992 and the ends of the stripes of connections 992. An outer boundary of the attachment area 994 is illustrated with dashed lines. Alternatively, any of the connections 992 can have various shapes. FIG. 9B illustrates a cross-sectional view of the embodiment of FIG. 9A.

FIG. 10A illustrates a portion of a wearable absorbent article 1070 with a portion of an absorbent core assembly 1075 joined to a portion of a stretchable outer cover 1071 over an attachment area 1094, according to embodiments of the present disclosure. The attachment area 1094 is formed by randomly distributed stripes of connections 1092, directly connecting the portion of the absorbent core assembly 1075 to the portion of the stretchable outer cover 1071, in a discontinuous manner, over the attachment area 1094. In alternative embodiments, stripes of connections can also be formed by spiral gluing, melt-blowing, printing adhesive patterns, or any other method of forming connection known to those of skill in the art. The connections 1092 are separated by unattached portions 1093 of the attachment area 1094. Despite the unattached portions 1093, the portion of the absorbent core assembly 1075 is considered joined to the portion of a stretchable outer cover 1071 over the entire attachment area 1094, because the portion of the stretchable outer cover 1071 is effectively constrained from relative movement with respect to the portion of the absorbent core assembly 1075, over the entire attachment area 1094. In FIG. 10A, the attachment area 1094 is defined by the extent of the stripes of connections 1092. An outer boundary of the attachment area 1094 is illustrated with dashed lines. Alternatively, any of stripes of connections 1092 can have various shapes. FIG. 10B illustrates a cross-sectional view of the embodiment of FIG. 10A.

The present disclosure includes wearable absorbent articles with absorbent core assemblies that are suitably joined to stretchable outer covers. While the absorbent core assemblies are provided with adequate structural integrity and support, the stretchable outer covers can also be extended to a significant degree because the absorbent core assemblies are joined to the stretchable outer covers by attachment areas that are strategically sized and placed within the articles. Thus, the wearable absorbent articles of the present disclosure can look attractive and feel comfortable while being less likely to leak.

The present disclosure contemplates that the various embodiments disclosed herein can be used in combination with various additional and/or alternate structures of absorbent articles, as will be understood by one of skill in the art.

Methods

Hysteresis Test

The following test methods utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

1. Select a 2.54 cm (width) 7.62 cm (length) sample of the material for testing. In some cases, if it is not be possible to get a 2.54 cm×7.62 cm sample, a smaller sample may be used, but a gage length of 25 mm must still be used. If the sample is activated or includes an activation portion, the length of the sample is taken in the direction of activation.

2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

3. Calibrate the tester according to the manufacturer's instructions.

4. Set the distance between the grips at 25 mm.

5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length ($l_{ini}$) which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.

6(a). First cycle loading: Pull the sample to a strain of 50% at a constant cross head speed of 254 mm/min.

6(b). First cycle unloading: Hold the sample at 50% strain for 30 seconds and then return the crosshead to its starting position (0% strain) at a constant cross head speed of 254 mm/min. Hold the sample in the unstrained state for 1 minute.

6(c). Set from second cycle loading: Pull the sample at a constant cross head speed of 254 mm/min, till it reaches a load of 0.05 N/25.4 mm (0.020 N/cm). Record the extended gauge length ($l_{ext}$). Next, return the crosshead to its starting position (zero strain) at a constant cross head speed of 254 mm/min. Set is defined as the strain at a second cycle load of 0.05 N/25.4 mm (0.020 N/cm). Calculate % set as indicated below.

6(d). Second cycle unload: Next, return the crosshead to its starting position (zero strain) at a constant cross head speed of 254 mm/min.

Percent Set is defined as the percent strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):

1. Loads at 25% strain and 50% strain (N/cm)

2. % set (Percent Strain measured at a second cycle load of 0.02 N/cm);

3. % set=$(l_{ext}-l_{ini})/l_{ini}*100\%$.

Five repetitions are done on each sample and the average and standard deviation reported.

Dimension Method

Various dimensions and ratios thereof are specified herein. Each dimension is measured according to the following method. All testing is performed in a conditioned room maintained at about 23 C±2 C and about 50%±2% relative humidity. Herein, width and length of the specimen are a lateral width and longitudinal length as defined herein. Precondition specimens at about 23 C±2 C. and about 50%±2% relative humidity for 2 hours prior to testing.

Prepare the article for testing as follows:

1. Lay the article on a substantially flat, horizontal surface.

2. Secure the article to the surface such that all process-induced contraction acting to foreshorten the absorbent core assembly is pulled out. For example, a pre-contracted waistband applied to the article or elastics along the longitudinal edges of the article and/or the absorbent core assembled may foreshorten the article laterally or respectively longitudinally, so any such process-induced contraction is pulled out. The article is secured to the flat, horizontal surface with clamps or adhesive tape capable of holding the absorbent core assembly with process-induced contraction pulled out.

3. Identify points between which widths and/or lengths of each attachment region, the absorbent core assembly, any unattached areas, and the article are to be measured, per definitions contained herein. This includes defining the hip region.

4. Measure each needed dimension to the nearest 1 mm using a steel ruler traceable to NIST.

5. Calculate any needed ratios as follows: Ratio=100%× [First Measurement/Second Measurement].

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable absorbent article comprising:
   an outer cover; and
   an absorbent core assembly, including a layer forming a top surface of the absorbent core assembly, a layer forming a bottom surface of the absorbent core assembly, and absorbent material disposed between the layers:
   wherein at least a portion of the outer cover is joined to the bottom surface of the absorbent core assembly over at least:
   a first attachment area, having a first area overall lateral width; and
   a second attachment area, wherein at least a portion of the second attachment area is disposed in a first hip region of the article;
   wherein the portion of the second attachment area that is disposed in the first hip region has a second area overall lateral width that is less than the first area overall lateral width;
   wherein the first hip region has an overall longitudinal length that is less than or equal to 30% of an overall pitch of the article; and
   wherein the first attachment area is disposed longitudinally outboard from the second attachment area.

2. The wearable absorbent article of claim 1, wherein the outer cover includes laterally stretchable areas disposed directly laterally outboard from the second attachment area.

3. The wearable absorbent article of claim 2, wherein the laterally stretchable areas are laterally elastic.

4. The wearable absorbent article of claim 1, wherein the outer cover includes laterally stretchable areas disposed directly laterally outboard from the first attachment area.

5. The wearable absorbent article of claim 4, wherein the laterally stretchable areas are laterally elastic.

6. The wearable absorbent article of claim 1, wherein at the first attachment area, the overall lateral width of the first attachment area is less than the overall lateral width of the absorbent core assembly.

7. The wearable absorbent article of claim 1, wherein at the first attachment area, the overall lateral width of the first attachment area is less than 95% of the overall lateral width of the absorbent core assembly.

8. The wearable absorbent article of claim 1, wherein the first attachment area is disposed adjacent to a waist edge of the article.

9. The wearable absorbent article of claim 1, wherein the first attachment area and the second attachment area are each disposed in a back of the article.

10. The wearable absorbent article of claim 1, wherein the first hip region has an overall longitudinal length that is less than or equal to 20% of an overall pitch of the article.

11. The wearable absorbent article of claim 1, wherein the first hip region is disposed longitudinally outboard from a farthest longitudinally outboard point of a leg opening edge of the article.

12. The wearable absorbent article of claim 1, wherein the second area overall lateral width is less than or equal to 80% of the first area overall lateral width.

13. The wearable absorbent article of claim 1, wherein the second attachment area has a substantially uniform overall lateral width.

14. The wearable absorbent article of claim 1, wherein substantially all of the second attachment area is disposed in a second hip region with an overall longitudinal length that is less than or equal to 30% of the overall pitch of the article.

15. The wearable absorbent article of claim 1, where at least one of the first attachment area and the second attachment area is substantially continuously joined to the outer cover.

16. The wearable absorbent article of claim 1, where the absorbent core assembly is directly connected to the outer cover through at least one of the first attachment area and the second attachment area.

17. The wearable absorbent article of claim 1, where the absorbent core assembly is durably connected to the outer cover through at least one of the first attachment area and the second attachment area.

18. The wearable absorbent article of claim 1, where the absorbent core assembly is refastenably connected to the outer cover through at least one of the first attachment area and the second attachment area.

19. The wearable absorbent article of claim 1, wherein at least a portion of the absorbent core assembly is joined to the outer cover by at least a third attachment area, having a third area overall lateral width that differs from the second area overall lateral width; wherein the third attachment area is longitudinally inboard to the second attachment area.

20. The wearable absorbent article of claim 1, which is a disposable wearable absorbent article.

* * * * *